US012761098B2

(12) United States Patent
Peter et al.

(10) Patent No.: US 12,761,098 B2
(45) Date of Patent: Oct. 13, 2026

(54) APPARATUS AND PROCESS FOR DETECTING A LEAK DURING ARTIFICIAL VENTILATION

(71) Applicant: Drägerwerk AG & Co. KGaA, Lübeck (DE)

(72) Inventors: Gerd Peter, Lübeck (DE); Bernd-Michael Dicks, Lübeck (DE); Tobias Heise, Lübeck (DE); Robert Jahns, Lübeck (DE); Martin Kroh, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 366 days.

(21) Appl. No.: 18/476,652

(22) Filed: Sep. 28, 2023

(65) Prior Publication Data

US 2024/0118160 A1 Apr. 11, 2024

(30) Foreign Application Priority Data

Oct. 5, 2022 (DE) ..................... 10 2022 125 601.4

(51) Int. Cl.

*G01M 3/02* (2006.01)
*A61M 16/00* (2006.01)
*G01M 3/00* (2006.01)
*G01M 3/40* (2006.01)

(52) U.S. Cl.

CPC ........ *G01M 3/002* (2013.01); *A61M 16/0003* (2014.02); *G01M 3/40* (2013.01); *A61M 2205/15* (2013.01)

(58) Field of Classification Search

None

See application file for complete search history.

(56) References Cited

U.S. PATENT DOCUMENTS

| | | | |
|---|---|---|---|
| 2,916,033 | A | 12/1959 | Coleman |
| 6,430,987 | B1 | 8/2002 | Stark |
| 7,882,835 | B2 | 2/2011 | Eger et al. |

(Continued)

FOREIGN PATENT DOCUMENTS

| | | | |
|---|---|---|---|
| DE | 29613243 | U1 | 10/1996 |
| DE | 10037380 | B4 | 3/2005 |

(Continued)

*Primary Examiner* — Erica S Lin

(74) *Attorney, Agent, or Firm* — McGlew and Tuttle, P.C.

(57) ABSTRACT

A device and a process detect a leak during artificial ventilation of a patient. A measurement system with a sensor arrangement and a sensor fluid guide unit is monitored. A fluid connection is established between a patient-side coupling unit and a medical device with a patient fluid guide unit. A gas sample is branched off from the patient fluid guide unit and guided through the sensor fluid guide unit to the sensor arrangement. A thermal conductivity time course of the gas sample reaching the sensor arrangement is determined with sensor arrangement measured values. Depending on a temporal change in the determined thermal conductivity, a decision is made as to whether there is an indication of a leak between the patient's fluid-guiding unit and the sensor arrangement. The leak establishes a fluid connection between the sensor fluid guide unit and/or the sensor arrangement and the environment.

13 Claims, 7 Drawing Sheets

(56) References Cited

U.S. PATENT DOCUMENTS

| | | | | |
|---|---|---|---|---|
| 8,221,530 | B2 | 7/2012 | Peter et al. | |
| 8,291,903 | B2 | 10/2012 | Maxeiner et al. | |
| 8,596,109 | B2 | 12/2013 | Stark et al. | |
| 10,010,691 | B2 | 7/2018 | Pessala et al. | |
| 2008/0176330 | A1* | 7/2008 | Asano | G01M 3/26 436/3 |
| 2008/0202526 | A1 | 8/2008 | Heinonen | |
| 2015/0273172 | A1* | 10/2015 | Pessala | A61M 16/0069 128/203.12 |
| 2015/0374947 | A1 | 12/2015 | Wallen | |
| 2021/0338950 | A1 | 11/2021 | Peter et al. | |
| 2023/0114548 | A1 | 4/2023 | Stark et al. | |

FOREIGN PATENT DOCUMENTS

| | | | |
|---|---|---|---|
| DE | 102005061439 | B3 | 5/2007 |
| DE | 102007046533 | B3 | 7/2008 |
| DE | 102009024040 | A1 | 12/2010 |
| DE | 102010014883 | A1 | 10/2011 |
| DE | 102014000101 | A1 | 7/2015 |
| DE | 102020002570 | A1 | 11/2021 |
| DE | 102020117607 | A1 | 1/2022 |
| DE | 102021126106 | A1 | 4/2023 |
| EP | 1961439 | B1 | 12/2009 |
| WO | 2014068000 | A1 | 5/2014 |

* cited by examiner

APPARATUS AND PROCESS FOR DETECTING A LEAK DURING ARTIFICIAL VENTILATION

CROSS REFERENCE TO RELATED APPLICATIONS

This application claims the benefit of priority under 35 U.S.C. § 119 of German Application 10 2022 125 601.4, filed Oct. 5, 2022, the entire contents of which are incorporated herein by reference.

TECHNICAL FIELD

The present invention pertains to a device and a process which are capable of automatically detecting a leak, in particular an abrupt leak, during artificial ventilation of a patient. During artificial ventilation, a gas sample is branched-off from a patient fluid guide unit and directed to a sensor arrangement, i.e. an arrangement which analyzes the gas sample. The leak can falsify (distort) measurements of the sensor arrangement.

SUMMARY

It is an object of the invention to provide a monitoring process for monitoring a measurement system wherein the measurement system is capable of examining a gas sample from a ventilation arrangement for the artificial ventilation of a patient and wherein the monitoring process is capable of automatically detecting a leakage relatively reliably. Furthermore, the invention is based on the object of providing a measurement system that is capable of examining a gas sample and automatically detecting a leak with relative reliability.

The object is attained by a monitoring process with monitoring process features according to the invention and by a measurement system with measurement system features according to the invention. Advantageous embodiments of the monitoring process according to the invention are, as far as useful, also advantageous embodiments of the measurement system according to the invention and vice versa.

The measurement system according to the invention is configured to be used during artificial ventilation of a patient. The patient is connected to a patient-side coupling unit or can be connected to a patient-side coupling unit at least temporarily. A breathing mask, tube, and catheter are examples of a patient-side coupling unit. At least temporarily during such artificial ventilation, a fluid connection is established between the patient-side coupling unit and a medical device. Preferably, the medical device is or comprises a ventilator that generates a gas mixture for artificial ventilation and delivers it through the fluid connection to the patient-side coupling unit. The medical device can also comprise a hand respiratory bag. The gas mixture contains oxygen and optionally at least one anesthetic. The fluid connection is established with the aid of a patient fluid guide unit.

The monitoring process according to the invention can be used to monitor such a measurement system. The monitoring process is performed while the fluid connection between the patient-side coupling unit and the medical device is established. The measurement system according to the invention is able to monitor itself for a leak.

The measurement system according to the invention comprises a sensor arrangement and a sensor fluid guide unit, the sensor fluid guide unit being at least temporarily in fluid connection with the patient fluid guide unit and with the sensor arrangement. The sensor arrangement comprises a thermal conductivity sensor and a signal processing unit.

The monitoring process according to the invention comprises the following automatically executed steps, and the measurement system according to the invention is configured to automatically perform the following steps:

At least temporarily, a negative pressure relative to an environment of the measurement system is established in the sensor fluid guide unit and/or the sensor arrangement.

A gas sample is branched-off (diverted) from the patient fluid guide unit and guided through the sensor fluid guide unit to the sensor arrangement. The negative pressure contributes to this. It is possible that the gas sample is extracted (sucked) from the patient fluid guide unit, for which purpose a negative pressure relative to the patient fluid guide unit is created. It is also possible that an additional positive pressure in the patient fluid guide unit relative to the environment causes the gas sample to be branched off.

A time course of the thermal conductivity of the gas sample is determined, which gas sample was branched off and reaches the sensor arrangement. This time course is determined using measured values of the thermal conductivity sensor and is referred to as the "thermal conductivity time course"

A decision is made as to whether an indication of a leak between the patient fluid guide unit and the sensor arrangement has occurred. This decision is made automatically by the signal processing unit depending on a temporal change (change over time, derivative with respect to time) in the determined thermal conductivity. Optionally, at least one further signal is used for the decision.

According to the invention, therefore, an indication of a leak is detected, or it is determined that no such indication is currently present. The leak for which an indication is determined or ruled out according to the invention at least temporarily establishes a fluid connection (fluid communication) between the sensor fluid guide unit and/or the sensor arrangement on the one hand and the environment of the measurement system on the other hand.

A "fluid guide unit" is understood to be a component that guides (conducts, directs) a fluid along a trajectory, where this trajectory is predetermined by the geometry, configuration, and arrangement of the component. A corrugated hose, a smooth hose, and a tube are examples of a fluid guide unit. The fluid guide unit does not necessarily include a conveying unit (pump/blower).

In many cases, reliable artificial ventilation of the patient requires that the time course of the concentration of at least one component of the gas mixture flowing through the patient fluid guide unit be measured with sufficient accuracy. In particular, the concentration is the fraction in vol-%. For example, the actual concentration time course is to follow a predetermined required concentration time course. The medical device is controlled accordingly, for which control the actual concentration time course must be measured reliably. The sensor arrangement is configured to measure an indicator of the actual concentration of the component. It is possible that the sensor arrangement is capable of measuring an indicator for the respective actual concentration of at least two components of the gas sample in each case.

According to the invention, a gas sample is branched off from the patient fluid guide unit, guided to the sensor arrangement, and examined by the sensor arrangement. The volume of the gas sample that is diverted and examined is generally small compared to the volume of the fluid that is in the patient fluid guide unit at any one time. Therefore, the monitoring process according to the invention and the measurement system according to the invention generally do not have a relevant influence on artificial ventilation of the patient. Preferably, the branched off gas sample is passed through the sensor arrangement and then fed back into the patient fluid guide unit.

A leak can falsify a measurement result of the sensor arrangement. Due to the negative pressure relative to the environment, ambient air can flow (penetrate) through this leak and reach the sensor arrangement, so that the sensor arrangement does not analyze the gas mixture from the patient fluid guide unit, but a generally unknown composition of this gas mixture and the ambient air. This can lead to an incorrect measurement result and therefore to incorrect artificial ventilation. In particular, a too low concentration of oxygen can be measured if the gas mixture has a higher oxygen concentration than the ambient air. It is therefore important to reliably and quickly detect an indication of a leak. If such an indication is detected, the measurement system can be checked more precisely automatically and/or manually, and the leak can then be eliminated—or it can be ruled out that a leak has actually occurred.

According to the invention, the thermal conductivity time course, i.e. the course of the thermal conductivity of the gas sample over time, is determined. For this determination, the thermal conductivity at a measuring position in the sensor arrangement or upstream from the sensor arrangement and downstream from a possible leak to be detected is used. The decision as to whether or not there is an indication of a leak is made as a function of the temporal change (derivative with respect to time) in the thermal conductivity.

It is possible to make the decision about the presence of a leak additionally depending on the measured time course of the concentration of a component in the branched off gas sample and/or the measured pressure course of the gas sample. According to the invention, the thermal conductivity time course is used in addition to or instead of a time course of the concentration of a component of the gas sample and/or the pressure of the gas sample. This feature has the following advantage: As a rule, a gas mixture with different components is guided through the patient fluid guide unit. Some of these components, in particular oxygen and carbon dioxide, also occur in the ambient air and therefore also in the environment of the patient fluid guide unit and in the environment of the measurement system. It is possible that the concentration of a component of the gas mixture in the patient fluid guide unit differs only slightly from the concentration of that component in the environment. For example, lung-protective artificial ventilation is sometimes used in which the concentration of oxygen in the supplied gas mixture is only relatively slightly above the concentration of oxygen in the air. Therefore, a leak changes the concentration of oxygen in the sensor fluid guide unit and in the sensor arrangement relatively little compared to a condition without a leak. In this case, the concentration of oxygen in the gas sample alone is not a sufficiently reliable indicator to detect a leak. In many cases, a relatively small leak also does not have a strong effect on the pressure in the patient fluid guide unit. In this case, the pressure alone is also not a reliable indicator. If detection of a leak were to rely solely on measuring the concentration of at least one gas sample component that is also present in the ambient air and/or on the pressure, there is a greater risk than with the monitoring process and with the measurement system of the invention that a leak would not be detected.

Another advantage of the invention is the following: If the detection of a leak would depend exclusively on the respective time course of the concentration of at least one component of the gas sample, the reliability of the detection may strongly depend on which components of the gas sample are chosen for monitoring. In this case, either such a monitoring process can only be used for certain situations. Or it may be necessary to measure in advance which components are present in the gas mixture in the patient fluid guide unit and whether their respective concentrations differ greatly from the concentration in the ambient air. The invention saves such a necessity and such a restriction.

In general, the pressure in the measurement system depends much more on the time-varying pressure prevailing in the patient fluid guide unit than on the pressure change due to a leak. One reason: In general, ventilation strokes are performed. Therefore, in many cases, the pressure is also not a suitable indicator for reliably detecting a leak.

The gas mixture that is guided through the patient fluid guide unit generally also contains components that do not occur at all or only at a significantly lower or even higher concentration in the ambient air. In particular, nitrogen usually occurs in the ambient air at a substantially higher concentration than in the gas mixture in the patient fluid guide unit. In contrast, usually neither an anesthetic nor nitrous oxide usually occurs with a relevant concentration in the environment. The commonly used anesthetics as well as nitrous oxide have a significantly lower thermal conductivity than air. Therefore, a leak usually significantly affects the thermal conductivity of the gas sample in the sensor arrangement. A temporal change in thermal conductivity is therefore usually a reliable indicator that a leak has occurred.

Even when there is no leak, the thermal conductivity of the gas mixture in the patient fluid guide unit, and thus in the branched off gas sample, usually varies over time. This is particularly true when the medical device used is a ventilator that performs a sequence of ventilation strokes, delivering a quantity of the gas mixture to the patient-side coupling unit in each ventilation stroke. Typically, the thermal conductivity oscillates as a function of these ventilation strokes. Therefore, according to the invention, a temporal change (variation) of the thermal conductivity is used rather than just an instantaneous conductivity value. This feature further increases the reliability that a leak is actually detected and reduces the risk of false alarms. In particular the reliability is increased that an oscillation of the thermal conductivity due to a leak is distinguished from an oscillation due to ventilation strokes, especially if a smoothing procedure is applied on the thermal conductivity time course. A special case of the thermal conductivity course or a sliding average is that the thermal conductivity ideally remains constant as long as no leak has occurred. The temporal change is then zero.

The thermal conductivity of the gas mixture in the patient fluid guide unit may also be altered (changed) by other events. Often, at least some of these events are deliberately induced, for example, because the medical device greatly increases or also decreases the concentration of a component of the gas mixture in the patient fluid guide unit in response to a user specification or a specification or command from a higher-level controller. For example, the concentration of oxygen is intentionally increased abruptly. Such an event can be detected or captured, for example by detecting a corresponding message from a control unit of the medical device, and taken into account when deciding whether or not there is an indication of a leak.

Both in known processes and devices for leak detection and in the monitoring process and measurement system according to the invention, a false alarm can be generated-more precisely, an indication of a leak is detected, although in reality no leak has occurred. On the one hand, it is usually important to reliably detect every leak, even if false alarms are then triggered. On the other hand, in many cases it is possible to verify whether or not a leak has actually occurred by carrying out a more detailed inspection after the indication of a leak has been detected.

As a rule, a leak to be detected causes a volume flow to occur through the leak, namely a volume flow from the environment to the sensor arrangement due to the negative pressure. In a preferred embodiment, a first indicator of a relative leak volume flow is repeatedly determined. As usual, a "volume flow" is understood to be the volume per unit time of a fluid flowing through a fluid guide unit or even through a leak. The relative leak volume flow according to the embodiment of the invention is the proportion (share) of the volume flow through the leak to the total volume flow to the sensor arrangement. The volume flow to the sensor arrangement is the sum of

- the volume flow at which the gas sample is branched off from the patient fluid guide unit and flows through the sensor fluid guide unit to the sensor arrangement, and
- the volume flow through the leak.

As a rule, the greater the relative leak volume flow is, the greater is the first indicator. In many cases, the total volume flow to the sensor arrangement and thus this sum remain constant over time, especially if the gas sample is branched off using a pump or other fluid conveying unit with a constant flow rate. However, a leak will change the relative leak volume flow.

According to a preferred embodiment, the first indicator of relative leak volume flow is determined as a function of the thermal conductivity time course measured by the sensor arrangement. In addition, the thermal conductivity of the environment (in general of ambient air) is specified and used. The thermal conductivity of ambient air is usually known and is specified. It is also possible to measure the thermal conductivity of the environment by the following process: For a short measurement period, a fluid connection is established between the sensor fluid guide unit and the environment, thus deliberately creating a leak. In one embodiment, the fluid connection between the sensor fluid guide unit and the patient fluid guide unit is interrupted at the same time. As a result, only ambient air is drawn to the sensor arrangement during the measurement period. During the measurement period, the thermal conductivity sensor of the sensor arrangement measures the thermal conductivity of the environment, e.g. ambient air, and not that of the gas mixture in the patient fluid guide unit.

Frequently, the total volume flow to the sensor arrangement is also known, especially if a pump or other fluid conveying unit or conveying unit draws in (sucks) the gas sample and the volume flow generated by the fluid conveying unit is known or measured, especially constant over time.

The decision as to whether or not an indication of a leak has occurred is made as a function of a temporal change (derivative with respect to time) of this first indicator of the relative leak volume flow, which is based on thermal conductivity.

Using an indicator of the relative leak volume flow has the following advantage over other possible approaches to using thermal conductivity to detect an indication of a leak: If a leak has occurred, the relative leak volume flow increases. If the first indicator is set such that the larger the relative leak volume flow is, the larger is the first indicator, then a leak will cause the first indicator to increase, otherwise the first indicator will decrease. This effect applies regardless of whether the leak increases or decreases the thermal conductivity of the gas sample flowing to the sensor arrangement, compared to a condition without a leak. In other words, this effect applies regardless of whether the ambient air or other gas mixture in the vicinity of the sensing system has a larger or a smaller thermal conductivity than the branched off gas sample. Therefore, this embodiment eliminates the need to specify or measure whether a leak increases or decreases thermal conductivity.

The decision as to whether an indication of a leak has occurred is made as a function of at) least a temporal change in that indicator of relative leak volume flow which depends on thermal conductivity.

Preferably, an indication of a leak is only detected if the first indicator deviates sufficiently strongly and for a sufficiently long time from a reference state. A lower time duration threshold and a lower change threshold are specified. An indication of a leak is detected if the following conditions are cumulatively fulfilled:

- The first indicator in a decision period differs from the first indicator in a reference period.
- The reference period is before (precedes) the decision period.
- Both the reference period and the decision period have a duration at least as long as the lower duration threshold.
- The deviation between the first indicator in the decision period and the first indicator in the reference period is at least as large as the lower change threshold.

Preferably, the thermal conductivity sensor continuously measures the thermal conductivity of the gas sample, and the decision period is a floating period ending, for example, at the current time, preferably a period of fixed duration.

In one embodiment, the first indicator is an estimate of the relative leak volume flow, for which a predetermined calculation rule is applied. For example, the first indicator is established in advance using the following assumption: The thermal conductivity of the gas mixture reaching the sensor arrangement is a weighted average of the thermal conductivity of the branched off gas sample and the thermal conductivity of the gas in the environment of the measurement system, usually ambient air. The weight factor by which the gas from the environment is included in the thermal conductivity of the gas mixture is the relative leak volume flow or depends on the relative leak volume flow. If there is no leak, then this weight factor is ideally zero. The thermal conductivity of the gas in the environment is specified or measured, e.g., as described earlier. According to the invention, the thermal conductivity of the gas mixture reaching the sensor arrangement is measured by the thermal conductivity sensor of the sensor arrangement. In one embodiment, the thermal conductivity of the branched off gas sample is measured at a time when it is determined that no leak has occurred, or measured in the medical device or patient fluid guide unit. Therefore, the relative leak volume flow is the only unknown in this context. The first indicator is the larger the greater the relative leak volume flow is, and is usually only an approximation for the actual relative leak volume flow.

According to the invention, the decision whether an indication of a leak has occurred is made depending on the measured thermal conductivity course of the gas sample reaching the sensor arrangement. Preferably, a first indicator of relative leak volume flow is used for this decision, the first indicator being based on thermal conductivity, for example according to the calculation procedure just mentioned. According to one embodiment, the temporal change (time variation) of the first indicator is used for the decision.

Preferably, the decision as to whether or not an indication of a leak has occurred is additionally made as a function of at least one further measurand. In a first alternative, the or at least one further measurand (measurement variable, measured variable) is the time course of the concentration of a component of the gas sample. This component is, for example, oxygen or carbon dioxide or nitrous oxide or an anesthetic (anesthetic agent). It is possible to use two different measurands, where each of the measurands is based on the time course of one component of the gas sample and each measurand relates to different components. It is also possible that the or at least one measurand is the time course of the summed concentrations of several components. In a second alternative, the further measurand is the time course of the pressure of the gas sample. These two alternatives can be combined with each other, so that the thermal conductivity and at least two further measured variables are used.

In one implementation, a second indicator of the relative leak volume flow is calculated depending on the concentration course and/or the pressure course. The decision whether an indication of a leak has occurred is made depending on a temporal change of the first indicator and a temporal change of the second indicator are used to decide.

In a first alternative, it is determined that an indication of a leak is present if both the thermal conductivity and the or at least one other measurand change, within a tolerance, at the same time and preferably lasting for at least one lower time duration threshold. With this alternative, there is less danger of triggering a false alarm. This alternative has the advantage that in some situations a changed thermal conductivity alone is not caused by a leak, but by a deliberately brought about event, for example by a deliberate change in the gas mixture provided by the medical device during artificial ventilation.

In a second alternative, it is determined that an indication of a leak exists if the thermal conductivity or the or at least one further measurand changes, but not necessarily both the thermal conductivity and the further measurand. This second alternative increases the certainty that every leak is actually detected.

A preferred embodiment of the measurement system according to the invention provides a measurement process and a sensor, which are capable of measuring both the thermal conductivity and the concentration of a component of the gas sample. The prerequisite is that the component is a paramagnetic gas and is present in the gas sample at a sufficiently large concentration. Oxygen is a paramagnetic gas that is in general contained in the gas mixture that is guided through the patient fluid guide unit to the patient-side coupling unit and the concentration of oxygen is to be measured in many cases anyway.

According to the embodiment, the following steps are performed, and the sensor arrangement is configured to perform the following steps:

The gas sample or at least a part (portion) of the gas sample is guided into a measuring chamber.

A magnetic field is applied to the measuring chamber. This magnetic field is applied in such a way that it has an oscillating field strength.

A heating element is heated. The heated heating element supplies thermal energy to the gas sample in the measuring chamber.

An electrical detection variable of the heating element is measured. The detection variable is in particular the electrical power consumed by the heating element, or the electrical voltage applied to the heating element. The detection variable correlates with the thermal conductivity of the gas sample in the measuring chamber.

Because the magnetic field has an oscillating field strength, the measured electrical detection variable also oscillates, synchronously with or at least depending on the oscillation of the magnetic field strength.

An oscillating signal and a further signal are derived. The oscillating signal oscillates depending on the magnetic field strength. The time course of the further signal does not depend on the oscillation of the magnetic field strength. To derive the two signals, filtering is applied to the electrical detection variable of the heating element.

The oscillating signal correlates with the time course of the concentration of the thermal conductivity of the paramagnetic gas in the gas sample and is used as an indicator of the time-varying concentration of the paramagnetic gas.

The further signal correlates with the thermal conductivity time course of the gas sample and is used as an indicator of the time-varying thermal conductivity of the gas sample. This is because the oscillation of the field strength of the applied magnetic field does not usually influence the thermal conductivity of the gas sample to a significant extent.

Compared to an embodiment in which a first sensor is used for thermal conductivity and a second sensor is used for concentration, this embodiment saves space and components. This is because multiple elements of the sensor arrangement can be used to measure both the thermal conductivity of the gas sample and the concentration of the paramagnetic gas. If the gas sample contains at least two different paramagnetic gases, this embodiment usually measures the sum of the concentrations of both gases.

In one embodiment, the step that an indication of a leak has been detected according to the invention triggers the step that an alarm is issued in at least one form that can be perceived by a human. In a preferred embodiment, however, a verification sequence is first triggered to verify whether or not a leak has actually occurred. The alarm is issued if the verification sequence provides the result with sufficient reliability that a leak has actually occurred. The verification sequence includes the following steps, which are performed automatically:

The step of branching off the gas sample and guiding it through the sensor fluid guide unit to the sensor arrangement is interrupted during the verification period. The sensor fluid guide unit is therefore not in fluid connection with the patient fluid guide unit during the verification period.

An indicator of the pressure in the sensor arrangement and/or in the sensor fluid guide unit is measured.

An indicator of the pressure in the patient fluid guide unit is measured.

The two measured pressures are compared with each other.

If the deviation between the two measured pressures meets a predefined criterion, it is determined that a leak is present. In particular, a decision is made that a leak is present if the deviations between the two pressures in a decision time period deviate from each other by more than a specified minimum threshold.

In the verification period, the sensor arrangement cannot measure the concentration of a component of the gas mixture flowing through the patient fluid guide unit. Thanks to the invention, the verification sequence only needs to be performed when an indication of a leak has been detected. Preferably, on the other hand, the verification sequence is performed while the indication of a leak has occurred, i.e., while the sensor arrangement is measuring the concentration of at least one component.

The invention further relates to a ventilation process and a ventilation arrangement which are capable of artificially ventilating a patient. The patient is connected to a patient-side coupling unit or can at least temporarily be connected to a patient-side coupling unit. The ventilation process comprises the step of delivering (conveying) a gas mixture from a medical device through a patient fluid guide unit to the patient-side coupling unit. The gas mixture comprises oxygen and optionally anesthetic (at least one anesthetic agent). The ventilation arrangement includes a medical device, a patient fluid guide unit, and the patient-side coupling unit, and is configured to convey a gas mixture from the medical device to the patient-side coupling unit.

The ventilation process is performed using a measurement system according to the invention, and the ventilation arrangement additionally comprises a measurement system according to the invention. A monitoring process according to the invention is used to decide whether an indication of a leak has occurred between the patient fluid guide unit and the sensor arrangement of the measurement system. The ventilation arrangement is capable of making such a decision automatically.

Advantageous embodiments of the verification process according to the invention are also advantageous embodiments of the ventilation process. Advantageous configurations of the measurement system according to the invention are also advantageous configurations of the ventilation arrangement.

In the following, the invention is described by means of an embodiment example. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
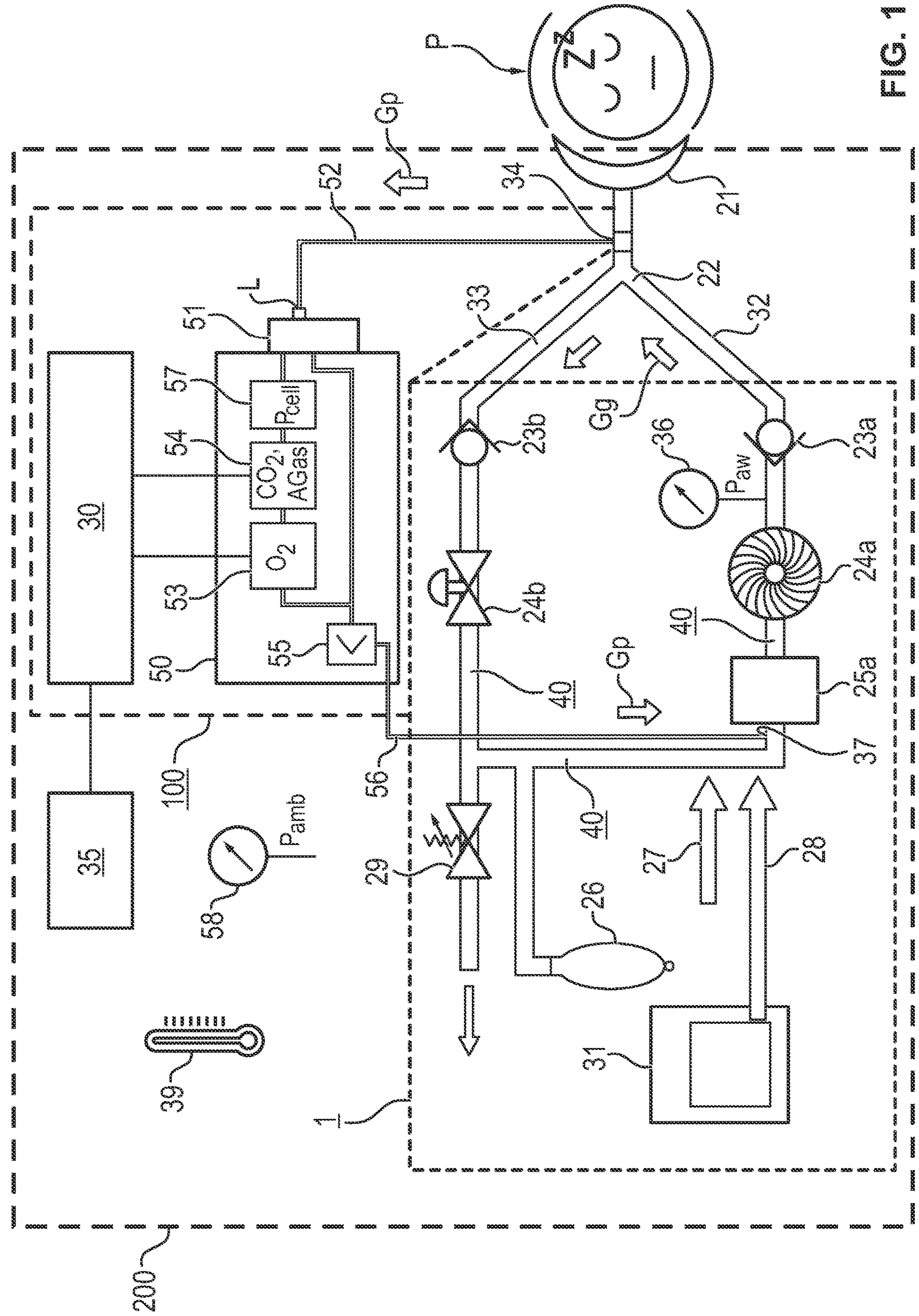
FIG. 1 is a schematic view of a ventilation circuit for artificial ventilation of a patient.

Referring to the drawings, FIG. 1 schematically shows a ventilation arrangement 200 with a schematically shown ventilation device (ventilator) 1, whereby the ventilation arrangement 200 is capable of artificially ventilating a patient P. Only the face of the patient P is shown schematically. The ventilator 1 maintains a ventilation circuit 40. In the embodiment example, the ventilator 1 is configured as an anesthesia device, and the patient P is anesthetized or at least sedated.

In the ventilation circuit 40, a gas mixture Gg is supplied to the patient P, which comprises oxygen ($O_2$), optionally carbon dioxide ($CO_2$), in the embodiment example at least one anesthetic agent, optionally a carrier gas for the anesthetic agent, and optionally further components. The air exhaled by the patient P preferably re-enters the ventilation circuit 40 and therefore does not enter the environment.

The invention can also be used for artificial ventilation in which a gas mixture Gg comprising oxygen is supplied to the patient P, but this gas mixture Gg does not comprise an anesthetic. The air exhaled by the patient P is therefore allowed to escape into the environment. Therefore, preferably, no ventilation circuit is implemented, but only a patient-fluid connection from the ventilator 1 to the patient P.

It is possible that artificial ventilation with or without anesthetic and patient P's own respiratory activity overlap. Patient P's own respiratory activity is brought about by the patient's respiratory musculature, namely through the patient's spontaneous breathing and optionally through external stimulation of the respiratory musculature.

A patient-side coupling unit 21, shown only schematically, for example a mouthpiece or a breathing mask or a tube, connects the patient P to the ventilation circuit 40 or to the patient-fluid connection. The patient-side coupling unit 21 is connected to a Y-piece 22. The Y-piece 22 is connected to a breathing gas line 32 for inhalation (inspiration) and to a breathing gas line 33 for exhalation (expiration).

A pump **24*a* draws in (sucks in) breathing gas and generates a continuous flow of breathing air through the inhalation breathing gas line 32 toward the Y-piece 22 and the patient-side coupling unit 21, and thus toward the patient P. Preferably, this pump 24*a* operates as a compressor that generates positive pressure and rotates at a speed in excess of 10,000 rpm. A carbon dioxide absorber ($CO_2$ absorber) 25*a* is capable of absorbing carbon dioxide ($CO_2$) from the ventilation circuit 40. A check valve (non-return valve) 23*a* allows gas to flow in the inspiratory breathing gas line 32 toward the Y-piece 22** and blocks gas flow in the reverse direction.

A check valve **23*b* allows gas flow in the exhalation breathing gas line 33 to flow away from the Y-piece 22 and blocks gas flow in the opposite direction. A controllable positive end-expiratory pressure (PEEP) valve 24*b*, depending on its position, allows the airflow generated by pump 24*a* to pass or blocks it, thereby contributing to the generation of the individual ventilatory breaths and determining the amplitudes and frequencies of these ventilatory breaths. The PEEP valve 24*b* also ensures that a sufficiently large air pressure is maintained in the lungs of the patient P, even at the end of the exhalation or when the ventilation circuit 40** is opened or interrupted for a short time. This reduces the risk of the patient P's lungs collapsing due to insufficient pressure.

A pressure relief valve 29 is able to relieve an overpressure in the ventilation circuit 40 by releasing breathing gas, preferably into a reforwarding line for anesthetic gas or also into the environment. This overpressure valve 29 is preferably configured as an "adjustable pressure limiting valve" and reduces the risk that the lungs of the patient P are damaged by an excessively high pressure, in particular in the case of manual ventilation by means of a breathing bag 26. The pressure threshold at which this overpressure valve 29 opens can be set manually from the outside and/or automatically by means of a control of the overpressure valve 29.

An anesthetic vaporizer 31 is capable of injecting a fluid stream 28 comprising a vaporous mixture of a carrier gas and at least one anesthetic into the ventilation circuit 40. The carrier gas preferably comprises oxygen. In addition, a fluid stream 27 of fresh air or other fresh gas can be supplied to the ventilation circuit 40.

The ventilation circuit 40 is kept running by the pump 24*a* and optionally by a breathing bag (hand respiratory bag) 26, which can be manually operated.

The pump 24*a*, the optional anesthetic vaporizer 31, the carbon dioxide absorber 25*a*, the check valves 23*a* and 23*b* as well as the valves 24*b* and 29 and the optional breathing bag 26 belong to a ventilator 1 shown only schematically, which can be configured as an anesthetic device. It is also possible that the ventilation circuit 40 is kept running solely with the aid of the breathing bag 26, for example on board a vehicle or in another location where no stationary power supply is available or where power supply has failed.

A signal-processing ventilation control unit (controller) 35, shown only schematically, receives measured values from a pressure sensor 58, which measures the air pressure $P_{amb}$ (ambient pressure) in the environment of the ventilation circuit 40, and a signal from an optional temperature sensor 39, which measures the ambient temperature. In addition, the ventilation control unit 35 receives measured values from a pressure sensor 36 that measures the current pressure in the ventilation circuit 40, for example the ventilation pressure (pressure in airway, $P_{aw}$) applied to the patient P, in one embodiment as a differential pressure relative to the ambient pressure $P_{amb}$. The ventilation control unit 35 controls the pump 24*a*, the anesthetic vaporizer 31, and other components of the ventilation circuit 40 in order to implement a desired artificial ventilation and optionally anesthetization of the patient P.

It is often desired that the gas mixture Gg, which is supplied to the patient P, fulfills a certain property. In particular, the concentration of a component of the gas mixture Gg should lie within a predetermined range. For example, the proportion of pure oxygen is to be in a predetermined range, for example between 40 vol-% and 50 vol-% or even between 25 vol-% and 30 vol-%. Or the proportion of anesthetic should be in a predetermined range. It is possible that this predetermined range is variable over time. In addition, the actual pressure of the gas mixture Gg should often follow a predetermined pressure time course (course over time).

In particular, for the control of the ventilator 1, it is necessary to measure the actual current concentration of carbon dioxide ($CO_2$) and/or oxygen ($O_2$) and/or nitrous oxide ($N_2O$) and/or pressure $P_{aw}$ and optionally of injected anesthetic, namely the concentrations and pressure $P_{aw}$ at a measuring position close to the patient-side coupling unit 21 and thus close to the mouth and/or nose of the patient P.

For this purpose, a sample containing breathing gas (hereinafter: a gas sample Gp) is diverted (branched off) from the ventilation circuit 40 via a gas sample fluid guide unit (sensor fluid guide unit) in the form of a sampling tube (sampling hose) 52, analyzed and fed back into the ventilation circuit 40 via a discharge tube (discharge hose) 56. The sampling tube 52 begins at a branch point 34 between the patient-side coupling unit 21 and the Y-piece 22. At the branch point 34 there is optionally a valve, not shown, which in the closed position disconnects the sampling tube 52 from the ventilation circuit 40 and which can be controlled by the ventilation control unit 35. When the valve is fully open or omitted, the sampling tube 52 is in unrestricted fluid connection with the ventilation circuit 40. The discharge tube 56 leads to a confluence point 37 upstream from the carbon dioxide absorber 25*a*.

The sampling tube 52 conducts the gas sample Gp to a sensor arrangement 50. This sensor arrangement 50 is spatially remote from the patient-side coupling unit 21 and also belongs, for example, to the schematically shown ventilator 1. In FIG. 1, the sensor arrangement 50 is shown outside the ventilator 1 for clarification. In the embodiment example, the sensor arrangement 50 comprises a pump 55 which sucks the gas sample Gp from the ventilation circuit 40 and draws it in through the sampling tube 52. Preferably, the pump 55 generates a permanent negative pressure on the side facing the sampling tube 52 and a permanent positive pressure on the side facing the discharge tube 56. The pump 55 is capable of generating a volume flow that is preferably constant over time and is, for example, 200 ml/min.

A sensor 54 is capable of generating signals that correlate with the respective concentration of $CO_2$, $N_2O$ and anesthetic in the branched-off gas sample Gp. Preferably, this sensor 54 comprises an infrared sensing head that exploits the dipole moment of molecules in the gas sample Gp and quantitatively evaluates the absorption of infrared active gases to determine the respective concentration. Preferably, the sensor 54 comprises a radiation source that emits electromagnetic radiation and a detector that measures an indicator of the intensity of impinging electromagnetic radiation and generates a corresponding signal. The radiation penetrates the gas sample Gp, and a gas to be detected absorbs a portion of the radiation.

A sensor 53 is capable of generating a signal that correlates with, among other things, the concentration of $O_2$ or other paramagnetic component(s) of the gas sample Gp. The sensor 53 is described in more detail below.

In one embodiment, the sampling tube 52 temporarily contains breathing air delivered to the patient P and temporarily breathing air exhaled by the patient P. In one embodiment, the rule of thumb is used that the proportion of oxygen in exhaled air is 5 vol % lower than the proportion of oxygen in the inhaled air.

It is possible that the sensor arrangement 50 comprises further concentration sensors, in particular to provide redundancy. In addition, the sensor arrangement 50 comprises a pressure sensor 57 that measures the pressure $P_{cell}$ of the gas sample Gp at the inlet of the sensor arrangement 50. This pressure $P_{cell}$ is time-varying because the pressure in the ventilation circuit 40 varies and because the sampling tube 52 is in fluid connection with the ventilation circuit 40 when there is no valve at the branch point 34 or as long as the optional valve at the branch point 34 is open. When the valve is omitted or open, the pressure in the ventilation circuit 40 propagates to the sensor arrangement 50 at approximately the speed of sound.

The sensor arrangement 50 with the pump 55, a signal processing unit 30 described below, a water trap 51 described below, the sampling tube 52 and the discharge tube 56 belong to a measurement system 100, which is schematically indicated in FIG. 1 and is part of the ventilation arrangement 200.

Figure 2:
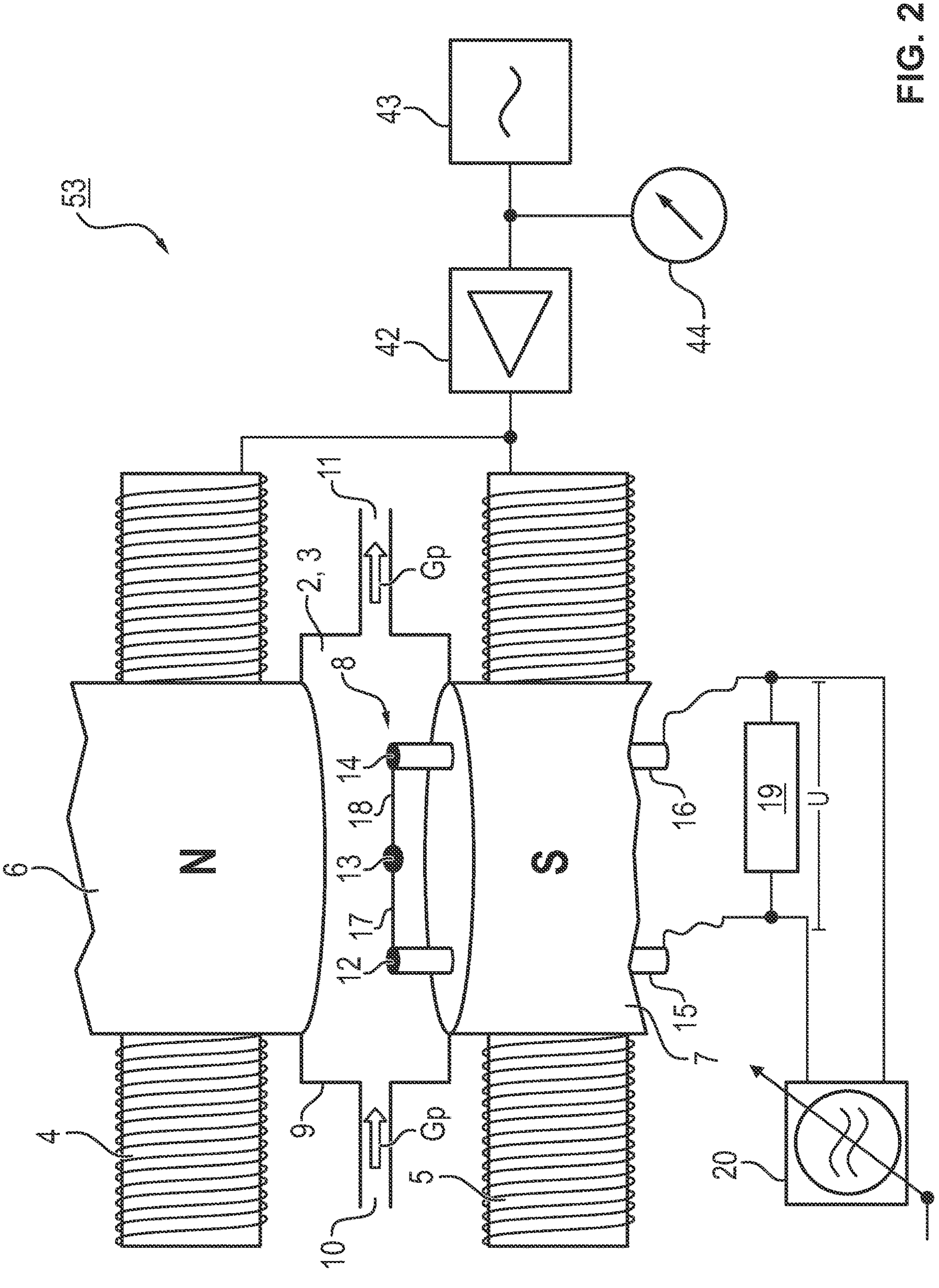
FIG. 2 is a schematic view of a first embodiment of a sensor that measures both the oxygen content and the thermal conductivity of the branched-off gas sample.

Referring to FIG. 2, a first embodiment of the oxygen sensor 53 is described below. The embodiment takes advantage of the fact that oxygen is a paramagnetic gas.

Two pole shoes (pole pieces) 6, 7 and two field coils 4, 5 generate a magnetic field. An air gap 3 occurs between the two pole shoes 6, 7 which gap 3 acts as a measuring chamber 2. This measuring chamber 2 is delimited by the two pole pieces 6, 7 and a wall 9. An inlet 10 and an outlet 11 are inserted into the wall 9. The gas sample Gp flows from the inlet 10 through the measuring chamber 2 to the outlet 11.

A thermocouple 8 is attached to two support wires 15, 16 at two junctions 12 and 14, the two support wires 15, 16 passing through the lower pole shoe 7 and being in thermal contact with the lower pole shoe 7. The thermocouple 8 comprises two wires 17, 18 connected together at a junction 13. A voltage source 20 applies an AC voltage to the two support wires 15, 16 and thus to the thermocouple 8. The flowing current heats the thermocouple 8 to a working temperature which is greater than the temperature of the gas sample Gp in the measuring chamber 2. A voltage U is measured at a measuring resistor 19. This voltage U contains an alternating current component and a direct current component.

The actual working temperature of the thermocouple 8 is measured at the junction 13. This temperature depends on the one hand on the voltage U which occurs between the support wires 15, 16 and on the other hand on the thermal conductivity of the gas sample Gp in the measuring chamber 2. A closed-loop control is carried out with the control gain (control objective) that the working temperature of the thermocouple 8 takes a constant value. The controlled (manipulated) variable is the time-varying voltage U which the voltage source 20 applies to the support wires 15, 16. Because the temperature of the thermocouple 8 remains the same, an electrical detection variable of the thermocouple 8 correlates with the thermal conductivity of the gas sample Gp in measurement chamber 2. It is possible that the applied electrical voltage U is itself the detection variable.

Another implementation to measure the detection variable is as follows: The time-varying electric power supplied to the thermocouple 8 is measured as the detection variable. The two support wires 15 and 16 are electrically connected to each other by the electrical measuring resistor 19. The electrical voltage U applied to this measuring resistor 19 is measured. An indicator of the magnitude of the electric current (amperage) flowing through the thermocouple 8 is also measured. As is well known, the electrical power depends on the voltage and the current strength.

A voltage source 43 is connected to the field coil 5 via a power amplifier 42, and the field coil 4 is connected to electrical ground. The voltage source 43 outputs an oscillating, in particular sinusoidal, electrical voltage. This voltage generates an oscillating, in particular sinusoidally varying magnetic field in the measurement chamber 2. The thermocouple 8, which is heated to a constant temperature, emits an amount of heat per unit time to the gas sample Gp in the measurement chamber 2. This amount of heat emitted per unit time correlates with the measured electrical power supplied to the thermocouple 8. Because the field strength of the magnetic field in the measuring chamber 2 oscillates periodically, the quantity of heat supplied per unit time also oscillates-provided that a paramagnetic gas is present as part of the gas sample Gp in the measuring chamber 2. The time course of the thermal conductivity contains a magnetically modulated thermal conductivity, which is a component that oscillates with the strength of the applied magnetic field. By appropriate filtering, two signals can be derived, namely an indicator of the magnetically modulated thermal conductivity and an indicator of the total thermal conductivity of the gas sample Gp.

Figure 3:
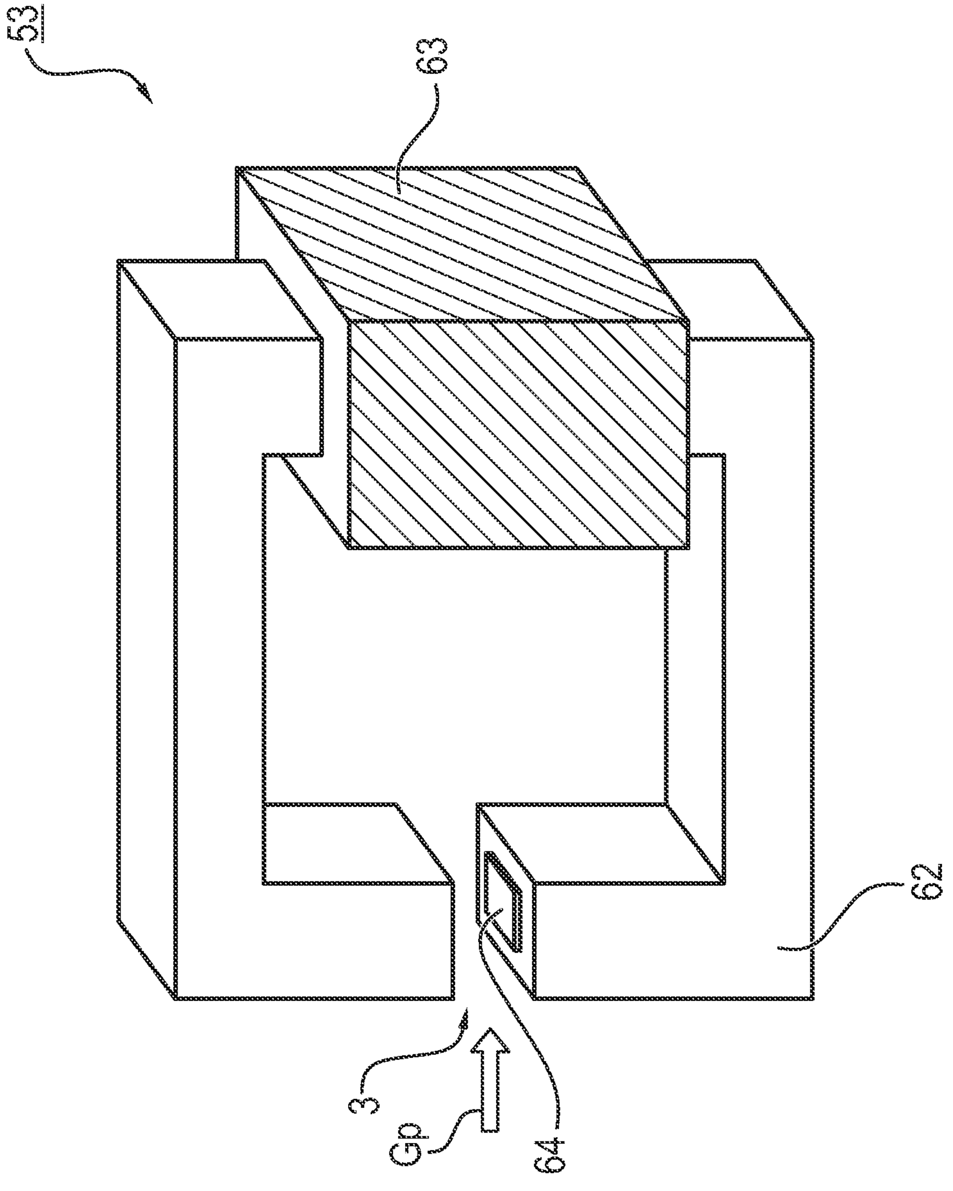
FIG. 3 is a schematic view of a second embodiment of such a sensor.
Figure 4:
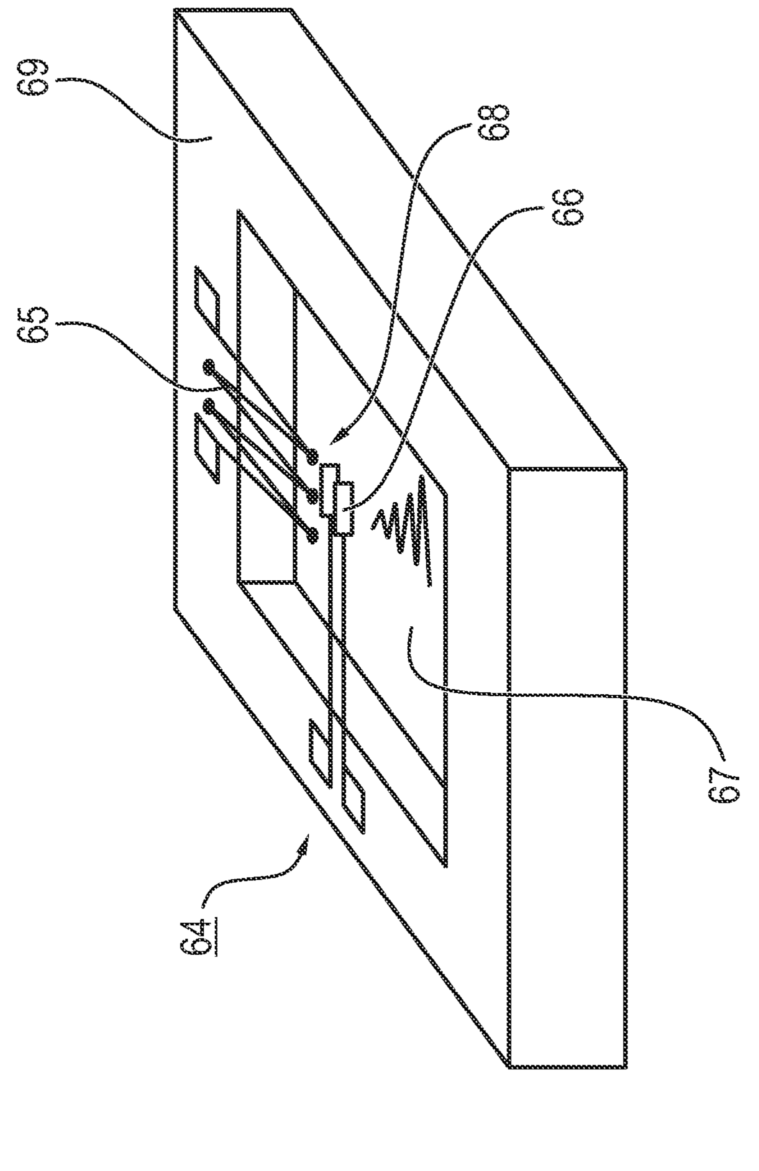
FIG. 4 is a perspective view showing the measuring unit of the sensor of FIG. 3.
Figure 5:
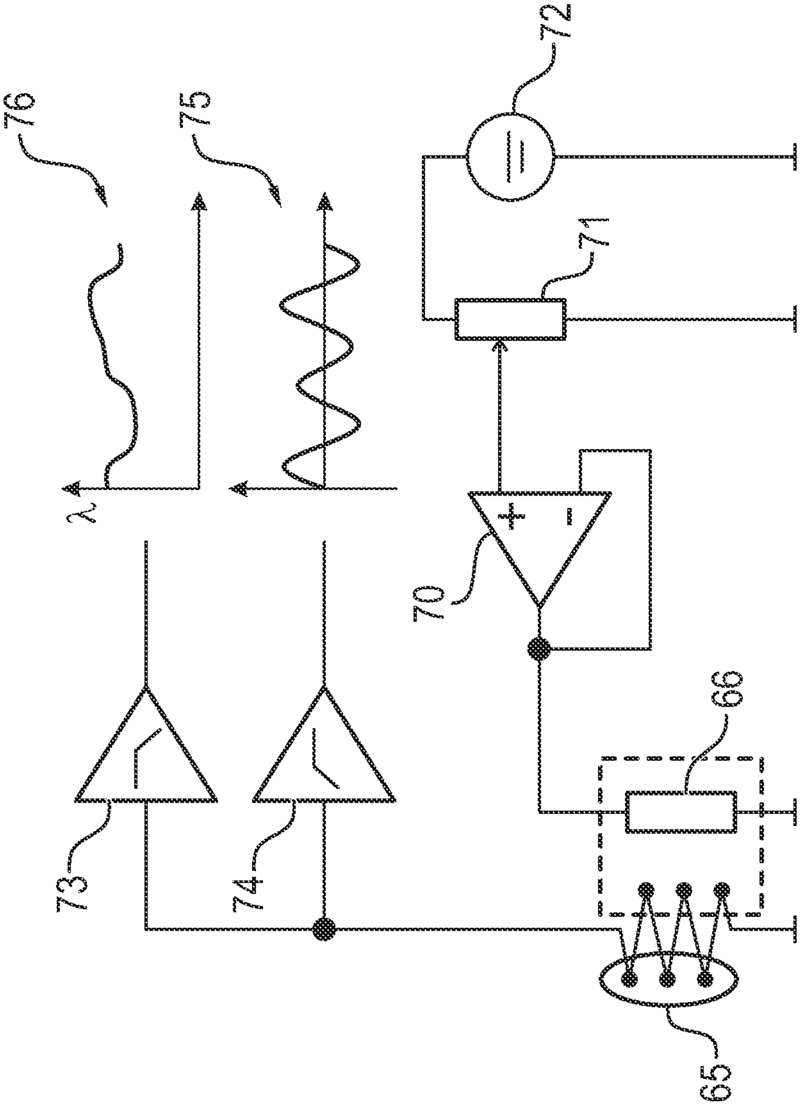
FIG. 5 is a circuit diagram showing an exemplary evaluation circuit of the sensor of FIG. 3.

FIG. 3, FIG. 4, and FIG. 5 show a further embodiment of the sensor 53. The same reference signs have the same meanings as in FIG. 2. The circuit of FIG. 5 can accordingly also be used for the embodiment according to FIG. 2.

An electromagnet 62 with an electric coil 63 generates a time-varying magnetic field in the air gap 3, cf. FIG. 3. A gas sample Gp to be examined reaches this air gap 3. The time course of the strength of the magnetic field generated is determined by the control of the coil 63. Preferably, the strength of the magnetic field has an oscillating, in particular sinusoidal course. A measuring unit 64 is arranged in the air gap 3, which is implemented as a chip, preferably as a semiconductor chip, which is manufactured using doped silicon, for example.

FIG. 4 shows the measuring unit 64 in detail. The measuring unit 64 comprises an electrically controllable heat conduction measuring element 65, an electrically controllable heating element 66 and a diaphragm (membrane) 67 in a frame 69. A gas sample Gp can pass through holes in the diaphragm 67 or around the diaphragm 67 to the elements 65, 66. The heating element 66 may be an electrically conductive resistive structure deposited on the diaphragm 67, or may be configured as a heating wire. The two elements 65 and 66 can also be configured as a one-piece element, which has a temperature-dependent electrical resistance.

The heating element 66 heats the measuring element 65 to a working temperature greater than the temperature of a gas sample Gp in the measuring chamber 2. The heated measuring element 65 measures the temperature at the measuring point 68. In the implementation shown, the measuring element 65 measures a thermoelectric voltage and exploits the Seebeck effect. The thermal conductivity of the gas sample Gp at the measuring point 68 changes synchronously with the time-varying magnetic field generated by the electromagnet 62, provided that the gas sample Gp at the measuring point 68 contains a paramagnetic gas with a sufficiently large concentration. A higher thermal conductivity results in a better dissipation of thermal energy. This in turn causes a lower temperature, which in turn causes a lower thermoelectric voltage.

FIG. 5 shows an example of an evaluation circuit with the following components:

- an amplifier 70 connected as an impedance converter,
- a voltage divider 71 with variable tap,
- a DC voltage source 72,
- a low-pass filter 73 and
- a high-pass filter 74 connected in parallel with the low-pass filter 73.

The heating element 66 is connected to the DC voltage source 72 via the amplifier 70 and the voltage divider 71. The output signal of the heat conduction measuring element 65 is fed through the low-pass filter 73 as well as the high-pass filter 74. An oscillating, in particular sinusoidal, i.e., periodically fluctuating signal 75 is present at the output of the high-pass filter 74. The oscillation of the signal 75 is determined by the oscillation of the applied magnetic field. The signal 75 correlates with the magnetically modulated thermal conductivity and thus with the proportion of paramagnetic gas, for example with the proportion of oxygen, in the gas sample Gp. At the output of the low-pass filter 73, a signal 76 is present which does not fluctuate (vary) periodically, or at least does not fluctuate as a function of the oscillation of the magnetic field, and correlates with the total thermal conductivity of the gas sample Gp.

The amount of heat per unit time comprises a superposition of a temporally constant portion and a periodically fluctuating portion. The periodically fluctuating portion correlates with the thermal conductivity and thus with the concentration of oxygen in the measuring chamber 2. The constant portion, i.e. the portion that does not oscillate with the strength of the magnetic field, correlates with the thermal conductivity of the entire gas sample Gp in the measuring chamber 2. The thermal conductivity of the oxygen and the respective thermal conductivity of each other component of the gas sample Gp contribute to this thermal conductivity of the gas sample Gp. Both components are measured. The sensor 53 thus supplies two signals:

- a periodically fluctuating signal which is an indicator of the concentration of oxygen or other paramagnetic gas in the measuring chamber 2 (periodically fluctuating component, alternating voltage, results from the magnetically modulated thermal conductivity) and
- a signal for the total thermal conductivity of the gas sample Gp in measuring chamber 2 (constant proportion, DC voltage).

Optionally, a measured value for the concentration of a component and/or for the thermal conductivity are displayed on a display device 44, cf. FIG. 2.

The pressure sensor 57 of the sensor arrangement 50 measures the total (entire) absolute pressure $P_{cell,abs}$ of the gas sample Gp. The quotient of a partial pressure and the total absolute pressure $P_{cell,abs}$ provides an indicator of the concentration of a component of the extracted gas sample Gp. In addition, the pressure sensor 57 provides an indicator of the pressure of the gas sample Gp.

Preferably, the pressure sensor 57 of the sensor arrangement 50 measures an absolute pressure $P_{cell,abs}$. In the following, the internal pressure in the sensor arrangement 50 relative to the ambient pressure $P_{amb}$ is used as the pressure $P_{cell}$, i.e. $P_{cell}=P_{cell,abs}-P_{amb}$. The relative pressure $P_{cell}$ can therefore also assume negative values, namely in the case of a negative pressure in the sensor arrangement 50 relative to the ambient pressure $P_{amb}$. Preferably, the relative pressure is measured several times during a breathing process, and a value calculated by suitable averaging over these measured values obtained during a breathing process is used as the pressure $P_{cell}$.

A signal processing unit 30 (control unit) shown schematically in FIG. 1 receives measured values from sensors of the sensor arrangement 50, in particular from the $CO_2$, $N_2O$ and anesthetic agent sensor 54, from the heat conduction and $O_2$ sensor 53, from the pressure sensors 57 and 58 and from other sensors, in particular from the temperature sensor 39, and automatically evaluates these measured values. Depending on the received and processed measured values, the signal processing unit 30 generates signals relating to the respective current concentration of $O_2$, $CO_2$, $N_2O$ and/or anesthetic agent and relating to the pressure $P_{cell}$ and transmits these signals to the ventilation control unit 35. The ventilation control unit 35 uses these received signals to automatically perform an open-loop control or closed-loop control for the ventilation circuit 40.

The gas sample Gp, which is preferably continuously sucked in by the pump 55, flows through a schematically shown water trap 51, which is arranged upstream of the sensors 53 and 54. This water trap 51 is configured with at least one gas-permeable membrane, this membrane preferably being made of a chemically inert material, e.g. polytetrafluoroethylene (PTFE). This water trap 51 can be constructed, for example, as described in DE 10 2007 046 533 B3 (corresponding U.S. Pat. No. 8,291,903 (B2) is incorporated by reference) or in DE 10 2009 024 040 A1 (corresponding U.S. Pat. No. 8,221,530 (B2) is incorporated by reference). In this way, the aspirated gas sample Gp is freed from condensate, particles, suspended matter, and germs. Liquid, in particular condensed-out water vapor, is retained by the membrane and flows into a tank of the water trap 51.

It is possible that a leak occurs on the path from the branch point 34 of the sampling tube 52 to the sensors 54 and 53, for example because the sampling tube 52 is not properly connected to the patient-side coupling unit 21, the Y-piece 22 or the water trap 51, or because material fatigue or contact or other mechanical influence from outside has led to a leak. This leak can occur abruptly, for example due to a mechanical influence or because artificial ventilation is started although two parts are mistakenly not connected fluid-tightly, or gradually, for example due to material fatigue. FIG. 1 shows an example of a leak L in the transition between the sampling tube 52 and the water trap 51.

Such a leak L can falsify the measurement results of sensors 53 and 54 and of optional further sensors. This is because a negative pressure occurs in the sampling tube 52 relative to the ambient pressure $P_{amb}$ and also relative to the pressure $P_{aw}$ in the ventilation circuit 40, at least during exhalation. This negative pressure results from the fact that the pump 55 of the measurement system 100 continuously extracts a gas sample Gp, and is, for example, 100 hPa. Ambient air can therefore be drawn through this leak L into the sampling tube 52 or into the sensor arrangement 50 because of the negative pressure relative to the environment. The negative pressure depends on the current and time-varying pressure in the ventilation circuit 40. Because the negative pressure in the sampling tube 52 varies relative to the ambient pressure $P_{amb}$, the amount of ambient air sucked in generally also varies over time in the event of a leak L.

The ambient air drawn in can, for example, simulate (feign) a higher or even a lower oxygen concentration in the ventilation circuit 40 than the actual oxygen concentration and therefore lead to an incorrect measurement. This false measurement could lead to an error in the artificial ventilation of the patient P. Therefore, a leak L must be detected as soon as possible, and a corresponding alarm must be issued in order to be able to locate and eliminate the leak L quickly. On the other hand, it is desired to generate as few false alarms as possible, ideally no false alarms are generated.

The following is an example of how such a leak L is detected. The term “volume flow” is used to describe the volume per unit of time that flows through a fluid guide unit. The following symbols are used:

| | |
|---|---|
| Vol'(50) | Known or measured volume flow generated by the pump 55 and with which a gas mixture Gg flows to the sensor arrangement 50, is preferably constant in time and is equal to the sum Vol'(40) + Vol'(env) |
| Vol'(40) | Volume flow extracted from the ventilation circuit 40 and flowing through the extraction tube 52, is equal to Vol'(50) in a leak-free state. |
| Vol'(env) | Volume flow sucked from the environment into the sampling tube 52 or into the sensor arrangement 50 when a leak L occurs and is zero in a leak-free state. |

-continued

| | |
|---|---|
| con(50) | Measured concentration of oxygen in the gas sample Gp reaching the sensor arrangement 50, is a weighted average of the concentrations con(40) and con(env) and is equal to con(40) in a leak-free state |
| con(40) | Concentration of oxygen in the ventilation circuit 40 at the branch point 34, is equal to con(50) in a leak-free state. |
| con(env) | Known concentration of oxygen in the ambient air, for example, is 20.95 vol %. |
| con(rel) | Indicator of the relative leak volume flow Vol'(rel), which is determined as a function of the oxygen concentration con(50) of the gas sample Gp, is equal to zero in a leak-free state. |
| Vol'(rel) | Relative leak volume flow |

Because the pump 55 of the sensor arrangement 50 draws (sucks) in the gas sample Gp, the leak L causes air to be drawn in from the environment in addition to the gas sample Gp from the ventilation circuit 40 and to reach the sensor arrangement 50. Therefore, a superposition of two volume flows reaches the sensor arrangement 50, namely a volume flow Vol'(40) from the ventilation circuit 40 through the sampling tube 52 (desired) and a volume flow Vol'(env) from the environment through the leak L (undesirable).

So the following applies:

$$Vol'(50)=Vol'(40)+Vol'(env) \quad (1)$$

The term "relative leak volume flow" Vol'(rel) refers to the proportion of the volume flow Vol'(env) through the leak L in the total volume flow Vol'(50) to the sensor arrangement 50, i.e.

$$Vol'(rel)=Vol'(env)/Vol'(50). \quad (2)$$

If no leak L has occurred, then Vol'(50)=Vol'(40) and Vol'(rel)=0. A rapidly occurring leak L leads to a rapid increase in the relative leak volume flow Vol'(rel).

Two different indicators of relative leak volume flow Vol'(rel) are described below. Both indicators are measured continuously to check whether a leak has occurred. Both indicators are each based on one measurand (measured variable). Ideally, the two indicators coincide, but in practice they differ from each other. The embodiment that at least two indicators are measured increases the reliability that each leak L is detected, and no false alarm is generated. The embodiment that at least two indicators are used for the relative leak volume flow Vol'(rel) has the following further advantage: When a leak occurs, the relative leak volume flow Vol'(rel) increases, regardless of whether the measurand itself increases or decreases due to the leak L.

In the embodiment, the one indicator is based on oxygen concentration and is denoted con(rel). In general, the volume flow of a component of a gas mixture through a fluid guide assembly is the product of the total volume flow through the fluid guide assembly and the proportion of the component in the gas mixture measured as vol %. The volume flow of oxygen into the sensor arrangement 50 results from a volumetric flow of oxygen from the ventilation circuit 40 and then, if a leak L has occurred, a volume flow of oxygen from the ambient environment through the leak L. Therefore, the volume of oxygen supplied per unit time is:

$$Vol'(50)*con(50)=Vol'(40)*con(40)+Vol'(env)*con(env)=[1-Vol'(rel)]*Vol'(50)*con(40)+Vol'(rel)-*Vol'*con(env). \quad (3)$$

By a transformation it follows that for the relative leak volume flow Vol'(rel) holds:

$$Vol'(rel)=Vol'(env)/Vol'(50)=[con(40)-con(50)]/[con(40)-con(env)]. \quad (4)$$

This equation is only ideally valid. The right-hand side is used as the first indicator of the relative leak volume flow Vol'(rel), i.e.

$$con(rel)=[con(40)-con(50)]/[con(40)-con(env)]. \quad (5)$$

The oxygen concentration con (env) in air is known and predetermined. The sensor 53 continuously measures the concentration con(50) of oxygen in the sensor arrangement 50.

In one embodiment, an oxygen sensor (not shown) measures the actual oxygen concentration con(40) in the ventilation circuit 40. Often, a desired oxygen concentration in the ventilation circuit 40 is predetermined. Depending on the predetermined desired oxygen concentration, oxygen is injected into the ventilation circuit 40. Optionally, an oxygen sensor (not shown) in the ventilator 1 measures the actual oxygen concentration con(40) in the injected gas mixture Gg. The predetermined or measured oxygen concentration is used as the oxygen concentration con(40). It is also possible that it is assumed that no leak L occurred at the beginning of artificial ventilation. Then con(50)=con(40) and Vol'(rel)=0. If a leak L suddenly occurs, the relative leak volume flow Vol'(rel) increases rapidly.

According to the implementation just described, the sensor 53 described above with reference to FIG. 2 to FIG. 5 continuously measures an indicator of the concentration con(50) of oxygen in the gas sample Gp that has been branched off and reaches the sensor arrangement 50. The sensor 53 may also employ another suitable measurement principle. Instead of the concentration of oxygen, the concentration of another component of this gas sample Gp can also be continuously measured.

According to the invention, the detection of a leak is not, or at least not only, based on the change in oxygen concentration. This is because a rapid change in the relative leak volume flow Vol'(rel) can also have a cause other than a leak, for example a deliberate change during artificial ventilation, in particular an occlusion during which the supply of respiratory air to patient P is interrupted for a very short time in order to measure one of patient P's vital parameters. Therefore, in the embodiment example, additionally a further time-varying property of the gas sample Gp is monitored. According to the invention, this further property is the relative thermal conductivity, and a rapid change in the measured relative thermal conductivity of the gas sample Gp is detected. It is also possible to base the monitoring of whether a leak has occurred solely on the thermal conductivity.

The following designations are used below:

| | |
|---|---|
| WLF(40) | Thermal conductivity of the gas sample Gp branched off from the ventilation circuit 40 through the sampling tube 52. |
| WLF(env) | Known or measured thermal conductivity of the ambient air |
| WLF(50) | Thermal conductivity of the gas sample Gp reaching the sensor arrangement 50, is measured by the sensor 53 |
| WLF(rel) | Indicator of the relative leak volume flow Vol'(rel), which is determined as a function of the thermal conductivity WLF(50) of the gas sample Gp. |

If no leak L has occurred, WLF(50)=WLF(40) and WLF(rel)=0 holds.

In one embodiment, it is assumed that the thermal conductivity WLF(50) of the gas sample Gp reaching the sensor arrangement 50 is a weighted average of the thermal conductivity WLF(40) of the gas sample Gp exhausted from the ventilation circuit 40 and the thermal conductivity WLF (env) of the ambient air. The weight factor for the thermal conductivity WLF(env) of the ambient air is the relative leak volume flow Vol'(rel), and the weight factor for the thermal conductivity of the gas mixture Gg in the ventilation circuit 40 is therefore 1−Vol'(rel).

$$WLF(50)=Vol'(rel)*WLF(env)+[1-Vol'(rel)]*WLF(40). \quad (6)$$

The indicator WLF(rel) for the relative leak volume flow Vol'(rel), which is based on the thermal conductivity, is ideally equal to Vol'(rel) and is calculated according to the following calculation rule, which is obtained by solving formula (6) for Vol'(rel):

$$WLF(rel)=[WLF(40)-WLF(50)]/[WLF(40)-WLF(env)]. \quad (7)$$

The thermal conductivity WLF(env) of dry ambient air is known, it is $\lambda$=0.02603 W/mK at 1 bar and 15 degrees C. The sensor 53 described with reference to FIG. 2 to FIG. 5 measures the thermal conductivity WLF(50) of the gas sample Gp which reaches the sensor arrangement 50. In one embodiment, the DC component (the constant component) of the voltage U applied to the thermocouple 8 of FIG. 2 or the DC component (signal 76) of FIG. 5 is used as an indicator of the thermal conductivity WLF(50). The thermal conductivity WLF(40) in the ventilation circuit 40 is usually significantly different from the thermal conductivity WLF (env) in the environment, so the denominator is not zero. For example, the thermal conductivity WLF(40) is measured by a sensor in the ventilator 1. In many cases, it is also justified to assume that there is no leak at the beginning of artificial ventilation and therefore WLF(40)=WLF(50) applies initially.

Figure 6:
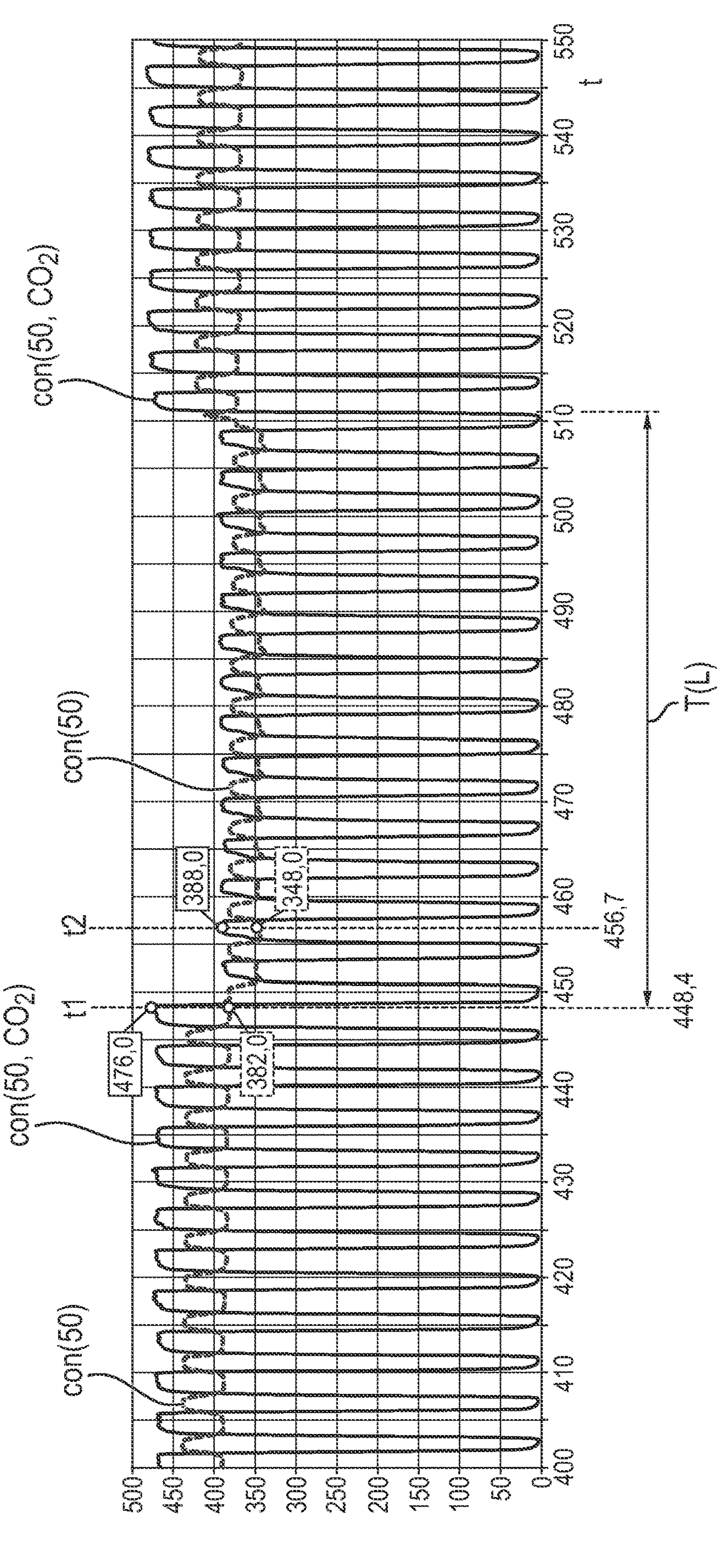
FIG. 6 is a graph of the time course of the oxygen concentration ($O_2$) and the $CO_2$ concentration in the gas sample taken as an example.
Figure 7:
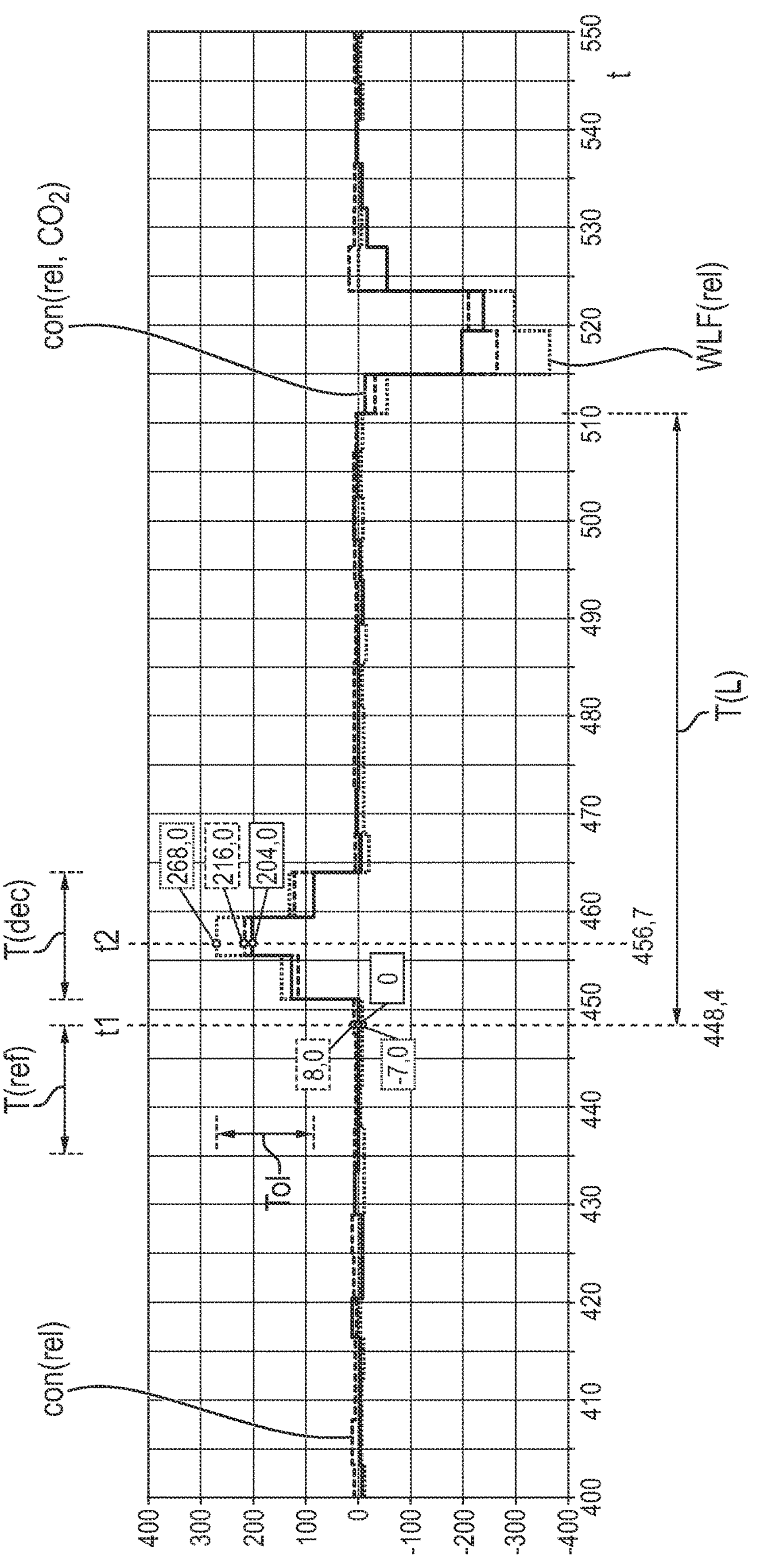
FIG. 7 is a graph showing as an example the time course of the three indicators of relative leak volume flow.

FIG. 6 and FIG. 7 show examples of test results obtained by the inventors in internal experiments. The time t is recorded on the x-axis in each case. In these internal experiments, the concentrations of $O_2$ and $CO_2$ as well as the thermal conductivity WLF were measured and used.

On the y-axis of FIG. 6 the time courses of the measured oxygen concentration con(50) and the measured carbon dioxide concentration con(50, $CO_2$) in the branched off gas sample Gp are plotted in 1/10 vol-%. The sensor 53 of FIG. 2 to FIG. 5 or another suitable sensor repeatedly measures the oxygen concentration con(50), the sensor 54 of FIG. 1 measures the carbon dioxide concentration con(50, $CO_2$). As can be seen, both the measured oxygen concentration con (50) and the measured carbon dioxide concentration con(50, $CO_2$) are lower in the period T(L) than in the rest of the measurement period. This observation is indicative of a leak L, but may also have another cause. As an example, the two respective measured values for the times t1=448.4 and t2=456.7 are entered.

As a rule, a leak L causes the thermal conductivity of the gas sample Gp reaching the sensor arrangement 50 to increase. One reason is that ambient air generally has a higher thermal conductivity than those components other than oxygen contained in the ventilation circuit 40. In individual cases, however, the leak may result in a lower thermal conductivity. The invention eliminates the need to make appropriate case discrimination and the required measurement.

In the example of FIG. 7, the time course of the following three indicators of relative leak volume flow Vol'(rel) are shown:

- the indicator con(rel), which is calculated according to the calculation rule (5),
- the indicator WLF(rel), which is calculated according to the calculation rule (7), and
- a further indicator con(rel, $CO_2$) for the relative leak volume flow Vol'(rel), which is calculated depending on the carbon dioxide concentration, for which a calculation rule analogous to calculation rule (5) is applied.

As can be seen in FIG. 7, all three measurements remain constant over time as long as no leak has occurred. This is because the ventilator 1 does not change the concentration of any component in the gas mixture Gg flowing through the ventilator circuit 40 during the period shown. Therefore, the thermal conductivity of the gas mixture Gg, and thus of the branched off gas sample Gp, also does not change. At the beginning of the period T(L) in which the leak L occurs, all three indicators change, and they change in the same direction and by approximately the same amount. At the beginning of the following period, all three indicators also change in the same direction.

The example of FIG. 7 shows three indicators for the relative leak volume flow Vol'(rel). According to the invention, at least one indicator of relative leak volume flow Vol'(rel) is used, preferably at least two indicators are used, namely an indicator WLF(rel) based on thermal conductivity and at least one indicator based on the concentration of a component of the gas sample Gp or on the pressure $P_{cell}$ (not shown) of the gas sample Gp in the sensor arrangement 50.

Ideally, the or each indicator of relative volume flow Vol'(rel) is equal to the actual relative leak volume flow. Ideally, then, at any time t con(rel)(t)=con(rel, $CO_2$)(t) =WLF(rel)(t)=Vol'(rel)(t).

As a rule, however, the indicator or each indicator differs from the actual relative leak volumetric flow Vol'(rel), in particular due to measurement errors and because the respective measurand propagates only at a limited speed. Therefore, in the embodiment example, the monitoring process described below is used to decide with greater certainty whether a leak L has actually occurred or not.

A minimum time period $\Delta T$ is specified. It is checked whether, in a decision period T(dec) which is at least as long as the minimum time period $\Delta T$, the indicators con(rel), con(rel, $CO_2$), WLF(rel) used for the relative leak volume flow Vol'(rel) cumulatively fulfill the following criteria:

- Throughout the decision period T(dec), each indicator con(rel), con(rel, $CO_2$), WLF(rel) increases relative to a reference period T(ref) preceding the decision period, where the absolute or relative increase is greater than a predetermined lower threshold.
- In the entire decision period T(dec), the indicators do not deviate from each other by more than a given threshold, either absolutely or relatively.

FIG. 7 shows an example of the decision period T(dec) and the preceding reference period T(ref). The decision period T(dec) is shorter than the period T(L) in which the leak L occurred. In addition, a tolerance band Tol is shown in FIG. 7. In the decision period T(dec), all three indicators lie within this tolerance band Tol. The width of this tolerance band Tol is specified.

According to the invention, at least one indicator of relative leak volume flow Vol'(rel) is determined and analyzed. Preferably, several indicators are compared with each other. This procedure detects an indication of a leak. This indication actually comes from a leak with a relatively high reliability. However, false alarms are possible, especially because an event other than a leak L significantly changes the relative leak volume flow Vol'(rel). It is therefore possible that an indication of a leak is detected, but in reality no leak has occurred.

In one embodiment, when an indication of a leak is detected as just described, an alarm is issued. A user can then check the fluid connections.

Preferably, however, a verification sequence is first performed and triggered automatically. If this verification sequence shows that a leak L has actually occurred, a corresponding alarm is output. However, this verification sequence causes the sensor arrangement 50 to be temporarily unable to supply any signals. Therefore, the verification sequence is preferably only carried out when an indication of a leak L is detected.

The verification sequence includes the following steps:

The pump 55 is switched off for the duration of the check.

An optional valve between the sampling tube 52 and the ventilation circuit 40 near the branch point 34 is opened or remains open.

Preferably, an optional valve not shown is closed between sensors 53 and 54.

If there is no leak, the pressure in the segment between the branch point 34 and the sensor 54 is equal to the pressure in the ventilation circuit 40, at least equal to the pressure near the Y-piece 22, see FIG. 1.

The pressure sensor 57 measures the pressure in this segment between the elements 34 and 54.

A pressure sensor (not shown), for example one in the ventilator 1, measures the pressure in the ventilation circuit 40.

If the two measured pressures differ by more than one tolerance, a leak L is detected and a corresponding alarm is generated. Otherwise, a leak can be excluded.

While specific embodiments of the invention have been shown and described in detail to illustrate the application of the principles of the invention, it will be understood that the invention may be embodied otherwise without departing from such principles.

| List of reference characters | |
|---|---|
| 1 | Ventilator, preferably anesthesia device |
| 2 | Measuring chamber of sensor 53, formed in air gap 3 |
| 3 | Air gap, provides the measuring chamber 2 |
| 4, 5 | Field coils, generate together with the pole shoes 6, 7 a magnetic field in the measuring chamber 2 |
| 6, 7 | Pole shoes, generate together with the field coils 4, 5 a magnetic field in the measuring chamber 2 |
| 8 | Thermocouple, includes wires 17, 18 and support wires 15, 16 |
| 9 | Wall of measuring chamber 2 |
| 10 | Inlet to measuring chamber 2 |
| 11 | Outlet from measuring chamber 2 |
| 12 | Connection point between the support wire 15 and the wire 17 |
| 13 | Junction between wires 17 and 18 |
| 14 | Connection point between the support wire 16 and the wire 18 |
| 15, 16 | Support wires for the thermocouple 8 |
| 17, 18 | Wires of the thermocouple 8, are connected to each other in the junction 13 |
| 19 | Measuring resistance of the thermocouple 8 |
| 20 | Voltage source |
| 21 | Patient-side coupling unit in the form of a mouthpiece or breathing mask, connected to the Y-piece 22 |
| 22 | Y-piece connecting the patient-side coupling unit 21 to a supply line for the supply of gas (inspiration) and a discharge line for the discharge of gas (expiration) |
| 23a | Check valve that allows gas flow in the direction of the patient P in the inhalation line 32 and blocks it in the opposite direction |

-continued

| List of reference characters | |
|---|---|
| 23b | Check valve that allows gas flow away from patient P in exhalation line 33 and shuts it off in the direction toward patient P |
| 24a | Blower generating a volume flow in the direction of the patient P |
| 24b | PEEP valve, which maintains a pressure in the patient's lungs P. |
| 25a | Carbon dioxide absorber, absorbs carbon dioxide from the ventilation circuit 40 |
| 26 | Breathing bag via which the ventilation circuit 40 can be driven |
| 27 | Fluid flow of fresh air or other fresh gas to the ventilation circuit 40 |
| 28 | Fluid flow of vaporous anesthetic to the ventilation circuit 40 |
| 29 | Adjustable pressure relief valve capable of releasing gas from the ventilation circuit 40 |
| 30 | Signal processing unit for the sensor arrangement 50, evaluates signals from the sensors 53, 54, 57 and 58, is able to detect a leak L and transmit a message to the ventilation control unit 35 |
| 31 | Anesthetic vaporizer, generates the anesthetic flow 28 |
| 32 | Breathing gas line for inhalation, connected to Y-piece 22, has check valve 23a |
| 33 | Breathing gas line for exhalation, connected to Y-piece 22, has check valve 23b |
| 34 | Branch point of the tapping hose 52 |
| 35 | Ventilation control unit, controls the pump 24a and the anesthetic vaporizer 31, receives signals about the respective gas concentration and messages from the signal processing unit 30, generates an alarm about an occurred leak L if necessary |
| 36 | Pressure sensor in the ventilation circuit 40, preferably measures the pressure P applied to the patient $P_{aw}$ |
| 37 | Confluence point, where the discharge tube 56 opens into the ventilation circuit 40, located upstream of the carbon dioxide absorber 25a |
| 40 | A ventilation circuit through which patient P is artificially ventilated includes patient-side coupling unit 21, Y-piece 22, inspiratory line 32, and expiratory line 33 |
| 42 | Power amplifier between the voltage source 43 and the field coil 5 |
| 43 | Voltage source, emits a sinusoidal electrical voltage |
| 44 | Optional display device of the sensor 53 |
| 50 | Sensor arrangement that measures the concentration of $O_2$, $CO_2$, $N_2O$, and optionally anesthetic agent includes sensors 51, 53, and 54, pump 55, and pressure sensor 57 |
| 51 | Water trap upstream of the sensor arrangement 50, comprises at least one membrane, preferably made of PTFE, and a tank |
| 52 | Extraction tube, through which a gas sample Gp is extracted from the ventilation circuit 40, begins at a branch point 34 between the patient-side coupling unit 21 and the Y-piece 22 and leads to the water trap 51 |
| 53 | Sensor for the $O_2$ concentration in the gas sample Gp, measures the concentration con(50) |
| 54 | Sensor for the concentration of $CO_2$, $H_2O$, and anesthetic in the gas sample Gp |
| 55 | Pump sucking a gas sample Gp into the sampling tube 52 |
| 56 | Discharge tube, through which a gas sample Gp is reintroduced into the ventilation circuit 40, leads to a confluence point 37 upstream from the carbon dioxide absorber 25a |
| 57 | Pressure sensor of the sensor arrangement 50, measures the pressure $P_{cell}$ |
| 58 | Ambient pressure sensor $P_{amb}$ |
| 62 | Electromagnet, generates a time-varying magnetic field in air gap 3, comprises coil 63 |
| 63 | Electric coil of the electromagnet 62 |
| 64 | Measuring unit, implemented as a chip, includes heat conduction measuring element 65, heating element 66, and diaphragm 67 |
| 65 | Electrically controllable heat conduction measuring element of measuring unit 64 |

List of reference characters

| | |
|---|---|
| 66 | Electrically controllable heating element of the measuring unit 64 |
| 67 | Measuring unit diaphragm 64 |
| 68 | Measuring point of the measuring unit 64 |
| 69 | Measuring unit frame 64 |
| 70 | Amplifier |
| 71 | Voltage divider |
| 72 | DC voltage source |
| 73 | Low-pass filter, provides at its output the signal 76 |
| 74 | High-pass filter, provides at its output the signal 75 |
| 75 | Signal at the output of the high-pass filter 74, correlated with the proportion of oxygen |
| 76 | Signal at the output of the low-pass filter 73, correlated with the thermal conductivity |
| 100 | Measurement system, includes sensor arrangement 50, signal processing unit 30, pump 55, sampling tube 52 and discharge tube 56 |
| 200 | Ventilation arrangement, includes the ventilator 1, the measurement system 100, the patient-side coupling unit 21, and the respiratory gas lines 32 and 33 |
| con(40) | Concentration of oxygen in the ventilation circuit 40 and thus in the gas sample Gp at the branch point 34, is detected or measured in a leak-free condition or in the ventilator 1, is equal to con(50) in a leak-free condition. |
| con(50) | Concentration of oxygen in the gas sample Gp reaching the sensor arrangement 50 is measured by the sensor 53, is equal to con(40) in a leak-free condition. |
| con($CO_2$) | Concentration of $CO_2$ in the gas sample Gp reaching the sensor arrangement 50 is measured by the sensor 53 |
| con(40, $CO_2$) | Concentration of $CO_2$ in the ventilation circuit 40 and thus in the gas sample Gp at the branch point 34. |
| con(env) | Concentration of oxygen in the ambient air, is given |
| con(rel) | Second indicator of the relative leak volume flow Vol'(rel), whichis determined as a function of the oxygen concentration con(50) of the gas sample Gp |
| Gg | Gas mixture delivered by the anesthesia device 1 to the patient-side coupling unit 21 |
| Gp | Gas sample, is branched off from the ventilation circuit 40, is guided through the sampling tube 52 to the sensor arrangement 50, and is fed back into the ventilation circuit 40 through the discharge tube 56 |
| L | A leak occurring both in the interval Ta and in the interval Tb between the ventilation circuit 40 and the sensor arrangement 50 and detected according to the invention |
| P | Patient being artificially ventilated and connected to the coupling unit 21 on the patient side |
| $P_{amb}$ | Pressure in the environment of the ventilation arrangement 200, measured by the pressure sensor 58 |
| $P_{aw}$ | Pressure in the breathing gas line 32 measured by the pressure sensor 58 |
| $P_{cell}$ | Pressure of the gas sample Gp at the inlet of the sensor arrangement 50, measured by the pressure sensor 57 |
| U | Electrical voltage between the support wires 15 and 16 |
| Tol | Tolerance band for the decision period T(dec) |
| T(L) | Period in which the leak L occurred |
| T(dec) | Decision time period in which the values of the indicators of relative leak volume flow used to decide on a leak lie |
| T(ref) | Previous reference period |
| Vol'(40) | Volume flow sucked out of the ventilation circuit 40 |
| Vol'(50) | Time constant total volume flow to sensor arrangement 50, equal to Vol'(40) + Vol'(env) |
| Vol'(env) | Volume flow passing through a leak L from the environment to the sensor arrangement 50. |
| Vol'(rel) | Relative leak volume flow, proportion of the volume flow Vol'(env) through a leak L to the total volume flow Vol'(50) to the sensor arrangement 50 |
| WLF(40) | Thermal conductivity of the gas sample Gp, is equal to the thermal conductivity in the ventilation circuit 40 at the branch point 34 |

List of reference characters

| | |
|---|---|
| WLF(50) | Thermal conductivity of the gas sample Gp reaching the sensor arrangement 50 is measured by the sensor 53 |
| WLF(env) | Thermal conductivity of the ambient air |
| WLF(rel) | First indicator of the relative leak volume flow Vol'(rel), which is determined as a function of the thermal conductivity WLF(50) of the gas sample Gp |

What is claimed is:

1. A monitoring process comprising the steps of:

providing a measurement system comprising a sensor arrangement and a sensor fluid guide unit;

carrying out the monitoring process while a patient is connected to a patient-side coupling unit and while, via a patient fluid guide unit, a fluid connection is established between the patient-side coupling unit and a medical device;

at least temporarily producing a negative pressure relative to an environment of the measurement system in at least one of the sensor fluid guide unit and the sensor arrangement;

branching off a gas sample from the patient fluid guide unit and guiding the branched off gas sample through the sensor fluid guide unit to the sensor arrangement;

by using measured values of the sensor arrangement, determining a thermal conductivity time course as a time course of thermal conductivity of the gas sample which reaches the sensor arrangement; and as a function of a temporal change of the determined thermal conductivity, determining whether an indication of a leak has occurred between the patient fluid guide unit and the sensor arrangement, wherein the leak establishes a fluid connection between at least one of the sensor fluid guide unit and the sensor arrangement on the one hand and an environment of the measurement system on the other hand.

2. A monitoring process according to claim 1, wherein:

the process comprises the further step of determining a time course of a first indicator for a relative leak volume flow, the determination is made depending on the thermal conductivity course and on a given thermal conductivity of the environment of the measurement system;

wherein the relative leak volume flow is the ratio between an induced volume flow through a leak to be detected and a total volume flow to the sensor arrangement; and the determination as to whether an indication of a leak has occurred is made as a function of the first indicator.

3. A monitoring process according to claim 2, wherein it is determined that an indication of a leak has occurred if in a decision time period, the decision time period having a time duration that is greater than a given lower duration threshold, the first indicator deviates more than a given lower threshold of change from the first indicator in a reference period, the reference period preceding the decision time period.

4. A monitoring process according to claim 1, wherein:

the process comprises the further step of determining one or more of a concentration time course as a time course of a concentration of a component of the gas sample and a pressure time course as a time course of a pressure of the gas sample, and the determination is made by using measured values of the sensor arrangement; and the determination as to whether an indication of a leak has occurred is additionally made as a function of one or more of a temporal change of the concentration and of a temporal change of the pressure.

5. A monitoring process according to claim 4, wherein:

the component of the gas sample is a paramagnetic gas; and the monitoring process comprises the further steps of:

directing the gas sample or at least a portion of the gas sample into a measuring chamber of the sensor arrangement;

with the sensor arrangement, applying a magnetic field with an oscillating field strength to the measuring chamber;

heating a heating element such that the heated heating element supplies heat energy to the gas sample in the measuring chamber;

measuring an electrical detection variable of the heating element;

filtering the electrical detection variable to derive an oscillating signal, which oscillates depending on the magnetic field strength, and to derive a further signal, which has a time course which does not depend on the oscillation of the magnetic field strength;

using the oscillating signal as an indicator of the concentration time course of the paramagnetic component of the gas sample; and using the further signal as an indicator of the thermal conductivity time course of the gas sample.

6. A monitoring process according to claim 4, wherein:

the monitoring process comprises the further steps of determining a time course of a first indicator for a relative leak volume flow, the determination is performed depending on the thermal conductivity course and on a given thermal conductivity of the environment of the measurement system;

wherein the relative leak volume flow is the ratio between an induced volume flow through a leak to be detected and a total volume flow to the sensor arrangement;

calculating a time course of a second indicator for a relative leak volume flow, the calculation is performed based on a concentration time course of the gas sample component or the course of the gas sample pressure and on a predetermined target concentration of the component or a pressure in the environment;

wherein the determination as to whether an indication of a leak has occurred is made as a function of a temporal change of the first indicator and as a function of a temporal change of the second indicator.

7. A monitoring process according to claim 6, wherein:

it is determined that an indication of a leak has occurred if the first indicator, in a decision time period having a time duration that is greater than a given lower duration threshold, deviates more than a given change threshold from the first indicator in a reference period that precedes the decision time period and if also the second indicator in the decision time period deviates from the second indicator in the reference period by more than the specified change threshold; and if, in the decision time period, the two indicators do not deviate from each other by more than a specified tolerance band.

8. A monitoring process according to claim 1, wherein if it is determined that an indication of a leak has occurred, a verification sequence is performed, the verification sequence comprising the steps of:

interrupting the step of guiding the gas sample through the sensor fluid guide unit to the sensor arrangement;

measuring an indicator of a pressure in the sensor arrangement;

measuring an indicator of a pressure in the patient fluid guide unit; and determining that a leak exists if a deviation between the two measured pressures meets a predetermined criterion.

9. A ventilation process for artificially ventilating a patient while the patient is connected to a patient-side coupling unit and while a fluid connection is established between the patient-side coupling unit and a medical device by means of a patient fluid guide unit, the ventilation process comprising the steps of:

providing a measurement system comprising a sensor arrangement and a sensor fluid guide unit;

conveying a gas mixture from the medical device through the patient fluid guide unit to the patient-side coupling unit;

branching off a gas sample from the patient fluid guide unit and guiding the branched off gas sample through the sensor fluid guide unit to the sensor arrangement; and determining whether an indication of a leak has occurred between the patient fluid guide unit and the sensor arrangement, the determination is made by a monitoring process comprising the steps of:

for branching off the gas sample from the patient fluid guide unit and guiding the branched off gas sample through the sensor fluid guide unit to the sensor arrangement, at least temporarily producing a negative pressure relative to an environment of the measurement system in at least one of the sensor fluid guide unit and the sensor arrangement;

by using measured values of the sensor arrangement, determining a thermal conductivity time course as a time course of thermal conductivity of the gas sample which reaches the sensor arrangement; and as a function of a temporal change of the determined thermal conductivity, determining whether the indication of a leak has occurred between the patient fluid guide unit and the sensor arrangement, wherein the leak establishes a fluid connection between at least one of the sensor fluid guide unit and the environment and the sensor arrangement and the environment.

10. A measurement system for monitoring artificial ventilation of a patient, wherein the patient is connected to a patient-side coupling unit or is at least temporarily connectable to the patient-side coupling unit, the measurement system comprising:

a sensor fluid guide unit; and a sensor arrangement, the sensor arrangement comprising:

a thermal conductivity sensor; and a signal processing unit, wherein a fluid connection between the patient-side coupling unit and a medical device via a patient fluid guide unit can be established or is established at least temporarily, wherein the measurement system is configured to create at least temporarily a negative pressure relative to an environment of the measurement system in at least one of the sensor fluid guide unit and the sensor arrangement, wherein the measurement system is configured to branch off a gas sample from the patient fluid guide unit and to guide the branched off gas sample through the sensor fluid guide unit to the sensor arrangement, wherein the thermal conductivity sensor is configured to determine a thermal conductivity time course as a time course of the thermal conductivity of the gas sample reaching the sensor arrangement, and wherein the signal processing unit is configured to determine, as a function of a temporal change of the determined thermal conductivity, whether an indication of a leak has occurred between the patient fluid guide unit and the sensor arrangement, wherein the leak establishes a fluid connection between at least one of the sensor fluid guide unit and the sensor arrangement on the one hand and the environment on the other hand.

11. A measurement system according to claim 10, wherein the signal processing unit is additionally configured to:

by using measured values of the sensor arrangement, determine at least one of a concentration time course as a time course of a concentration of a component of the gas sample and a pressure time course as a time course of a pressure of the gas sample; and to determine that an indication of a leak has occurred as a function of a temporal change of at least one of the determined concentration and the determined pressure.

12. A measurement system according to claim 11, wherein:

the component of the gas sample is a paramagnetic gas; and the thermal conductivity sensor comprises: a measuring chamber; a magnetic field generator; and a heating element;

the magnetic field generator is configured to apply a magnetic field with an oscillating field strength to the measuring chamber;

the sensor arrangement is configured to direct the gas sample or at least a portion of the gas sample into the measuring chamber and to heat the heating element;

the heated heating element is configured to supply thermal energy to the gas sample in the measuring chamber;

the thermal conductivity sensor is configured to measure an electrical detection variable of the heating element; and the sensor arrangement is configured to derive an oscillating signal which oscillates depending on the magnetic field strength, and to derive a further signal with a time course that does not depend on the oscillating magnetic field strength, by means of a filtering of the electrical detection variable, and to use the oscillating signal as an indicator of the concentration time course of the paramagnetic component of the gas sample, and to use the further signal as an indicator of the thermal conductivity time course of the gas sample.

13. A ventilation arrangement for artificial ventilation of a patient, the ventilation arrangement comprising:

a patient fluid guide unit;

a patient-side coupling unit configured to be connected to a patient;

a medical device configured to deliver a gas mixture from the medical device through the patient fluid guide unit to the patient-side coupling unit; and a measurement system for monitoring artificial ventilation of the patient, the measurement system comprising:

a sensor fluid guide unit; and a sensor arrangement, the sensor arrangement comprising:

a thermal conductivity sensor; and a signal processing unit, wherein a fluid connection between the patient-side coupling unit and the medical device via the patient fluid guide unit can be established or is established at least temporarily, wherein the measurement system is configured to create at least temporarily a negative pressure relative to an environment of the measurement system in at least one of the sensor fluid guide unit and the sensor arrangement, wherein the measurement system is configured to branch off a gas sample from the patient fluid guide unit and to guide the branched off gas sample through the sensor fluid guide unit to the sensor arrangement, wherein the thermal conductivity sensor is configured to determine a thermal conductivity time course as a time course of the thermal conductivity of the gas sample reaching the sensor arrangement, and wherein the signal processing unit is configured to determine, as a function of a temporal change of the determined thermal conductivity, whether an indication of a leak has occurred between the patient fluid guide unit and the sensor arrangement, wherein the leak establishes a fluid connection between at least one of the sensor fluid guide unit and the environment and the sensor arrangement and the environment.

* * * * *